(12) United States Patent
Jolly et al.

(10) Patent No.: US 12,708,728 B2
(45) Date of Patent: Aug. 18, 2026

(54) TRACHEAL TUBE ASSEMBLY

(71) Applicant: Passy-Muir, Inc., Irvine, CA (US)

(72) Inventors: Cameron Jolly, Newport Beach, CA (US); Jose Comino, Irvine, CA (US); Daniel Carrillo, Irvine, CA (US)

(73) Assignee: Passy-Muir, Inc., Irvine, CA (US)

( * ) Notice: Subject to any disclaimer, the term of this patent is extended or adjusted under 35 U.S.C. 154(b) by 566 days.

(21) Appl. No.: 18/176,988

(22) Filed: Mar. 1, 2023

(65) Prior Publication Data

US 2024/0293632 A1 Sep. 5, 2024

(51) Int. Cl.
*A61M 16/04* (2006.01)
*A61M 16/08* (2006.01)
*A61M 25/06* (2006.01)

(52) U.S. Cl.
CPC .... *A61M 16/0465* (2013.01); *A61M 16/0488* (2013.01); *A61M 16/0816* (2013.01); *A61M 2025/0681* (2013.01)

(58) Field of Classification Search
CPC ........... A61M 16/0465–0486; A61M 16/0816; A61M 2025/0681
See application file for complete search history.

(56) References Cited

U.S. PATENT DOCUMENTS 3,334,631 A 8/1967 Stebleton
3,688,774 A 9/1972 Akiyama
4,315,505 A 2/1982 Crandall et al.
4,817,598 A * 4/1989 LaBombard ...... A61M 16/0497 128/207.14
D585,980 S 2/2009 Cabrera
D586,459 S 2/2009 Cabrera
D599,006 S 8/2009 Cabrera
(Continued)

FOREIGN PATENT DOCUMENTS

BR PI 1008261 A2 3/2016
EM EU 005432507 7/2018
(Continued)

OTHER PUBLICATIONS

Written Opinion mailed Feb. 26, 2025 in International Application No. PCT/US2024/017263, in 12 pages.
(Continued)

*Primary Examiner* — Rachel T Sippel
(74) *Attorney, Agent, or Firm* — Knobbe, Martens, Olson & Bear, LLP

(57) ABSTRACT

A tracheostomy tube assembly is proposed. The assembly may include an outer cannula configured to be positioned in an airway. The assembly may also include an outer cannula connector coupled to a proximal end of the outer cannula, the outer cannula connector including a proximal region. The proximal region of the outer cannula connector may include a cutout extending in a direction of a length of the outer cannula connector. The assembly may further include an inner cannula configured to be disposed inside the outer cannula. A proximal region of the inner cannula may include a grip protrusion configured to be gripped by a finger of a user. The grip protrusion may be accommodated at least partially in and exposed by the cutout of the outer cannula connector when the inner cannula is inserted into the outer cannula via the outer cannula connector.

26 Claims, 30 Drawing Sheets

(56) References Cited

U.S. PATENT DOCUMENTS

| | | | | |
|---|---|---|---|---|
| D695,390 | S | 12/2013 | Bruggeman et al. | |
| D858,747 | S | 9/2019 | Ramdohr | |
| 12,029,584 | B2 | 7/2024 | Najdahmadi | |
| 2005/0166924 | A1 | 8/2005 | Thomas et al. | |
| 2007/0083262 | A1 | 4/2007 | Matlock | |
| 2009/0064999 | A1* | 3/2009 | Marten | A61M 16/0429 128/200.26 |
| 2012/0160238 | A1 | 6/2012 | Matlock et al. | |
| 2012/0199120 | A1 | 8/2012 | Matlock | |
| 2012/0204882 | A1 | 8/2012 | Hayman | |
| 2013/0081634 | A1 | 4/2013 | Kiernan et al. | |
| 2014/0034048 | A1 | 2/2014 | Bruggeman et al. | |
| 2014/0238389 | A1 | 8/2014 | Bruggeman et al. | |
| 2014/0360495 | A1 | 12/2014 | Traeger et al. | |
| 2015/0136123 | A1 | 5/2015 | Donlon et al. | |
| 2018/0043118 | A1 | 2/2018 | Jeffrey et al. | |
| 2018/0133425 | A1* | 5/2018 | Bateman | A61M 16/04 |
| 2018/0169362 | A1* | 6/2018 | Bateman | A61M 16/0427 |
| 2019/0076609 | A1 | 3/2019 | Donlon et al. | |
| 2019/0143062 | A1 | 5/2019 | Traeger et al. | |
| 2019/0184120 | A1 | 6/2019 | Ramdohr et al. | |
| 2023/0141119 | A1 | 5/2023 | Veasey et al. | |

FOREIGN PATENT DOCUMENTS

| | | | |
|---|---|---|---|
| JP | 2015-124912 | A | 7/2015 |
| JP | 2015-523188 | A | 8/2015 |
| WO | WO 1996/036386 | A1 | 11/1996 |

OTHER PUBLICATIONS

International Search Report and Written Opinion mailed May 15, 2024 in International Application No. PCT/US2024/017263, in 18 pages.

Notice of Allowance dated Aug. 15, 2024 in U.S. Appl. No. 29/871,907.

Notice of Allowance dated Jun. 26, 2024 in U.S. Appl. No. 29/871,906.

International Preliminary Report on Patentability dated May 16, 2025 in International Application No. PCT/US2024/017263, in 21 pages.

Tracheostomy care. Available online 2024. Retrieved Jun. 14, 2024 from URL: https://passy-muir.com/tracheostomy_care/.

Office Action dated Jun. 27, 2024 in U.S. Appl. No. 29/871,907.

Office Action dated Jan. 27, 2026 in Japanese Application No. 2025-534427, in 5 pages.

Office Action dated Apr. 1, 2026 in Brazilian Application No. BR112025013052-8.

* cited by examiner

TRACHEAL TUBE ASSEMBLY

CROSS-REFERENCE TO RELATED APPLICATIONS

This application is concurrently filed with U.S. Design Application entitled "INNER CANNULA FOR TRACHEAL TUBE ASSEMBLY" and U.S. Design Application entitled "TRACHEAL TUBE ASSEMBLY", the entire contents of each of which are incorporated herein by reference in their entirety.

BACKGROUND

Technical Field

The described technology generally relates to a tracheal tube assembly (hereinafter to be interchangeably used with a "tracheostomy tube assembly," "tracheostomy tube(s)" or "tracheal tube(s)").

Description of Related Technology

Tracheal tubes may be used to create an artificial airway to allow for or control the flow of air or other gases through a patient's trachea or windpipe. Such tracheal tubes may include tracheostomy tubes. Tracheostomy tubes are typically used for prolonged ventilation, as the use of a tracheostomy tube may be more comfortable for a patient. A typical tracheostomy tube is generally inserted into the trachea via a surgical incision in the neck, or through a bedside percutaneous dilation procedure. After insertion of the tube into the trachea, a portion of the tracheostomy tube remains outside the patient.

SUMMARY

The embodiments disclosed herein each have several aspects no single one of which is solely responsible for the disclosure's desirable attributes. Without limiting the scope of this disclosure, some example features and combinations will now be briefly discussed. After considering this discussion, and particularly after reading the section entitled "Detailed Description," one will understand how the features of the embodiments described herein provide advantages in connection with finger-occluding a tracheostomy tube.

One aspect is a tracheostomy tube assembly including an inner cannula that may be easily removed from an outer cannula or an outer cannula connector (or a hub).

Another aspect is a tracheostomy tube assembly including an outer cannula connector and an inner cannula that will not interfere with other devices (e.g., speaking valve, heat and moisture exchanger, etc.) connected to the outer cannula connector, that enables patients to digitally occlude the tracheostomy tube, with an inner cannula that may be removed or installed with ease and without excessive forces applied to the outer cannula connector.

In a non-limiting example, a proximal region of the outer cannula connector may include one or more cutouts that allow for easy insertion and removal of the inner cannula into and from the outer cannula connector.

In a non-limiting example, the outer cannula connector may include a tapered region that can facilitate removal and insertion of the inner cannula by hand, and to prevent interference with devices connected to the outer cannula connector.

In a non-limiting example, the inner cannula may include one or more grip protrusions that can facilitate gripping of a proximal region thereof through the cutouts in the outer cannula connector so as to compress the inner cannula at the region of the cutouts prior to insertion and removal of the inner cannula. Further, the insertion or removal of the inner cannula may be done by hand in a manner that does not disturb the outer cannula or outer cannula connector placed on a patient.

In a non-limiting example, the one or more grip protrusions of the inner cannula may partially or fully fill the cutouts in the outer cannula connector making the outer cannula connector a unified standard 15 mm hub when the inner cannula is inserted.

In a non-limiting example, the proximal region of the inner cannula may be smaller in diameter than the widest portion of the outer cannula connector, except for a face portion of the inner cannula that is larger than the proximal end of the outer cannula connector. In this example, the outer cannula connector may form a connector portion for attachment to upstream medical tubing and/or devices, but the face portion of the inner cannula may be uninterrupted to enable digital occlusion.

In a non-limiting example, the proximal region of the inner cannula may be smaller in diameter than the widest portion of the outer cannula connector including the face portion of the inner cannula that rests upon a ridge or lip crevice at the further proximal end of the outer cannula. In this example, the outer cannula connector may form a structure for attachment to upstream medical tubing and/or devices, but the inner cannula seals the cutouts in the outer cannula connector while providing uninterrupted surface at the front of the device to enable digital occlusion.

BRIEF DESCRIPTION OF THE DRAWINGS

The foregoing and other features of the disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

DETAILED DESCRIPTION

Figure 1:
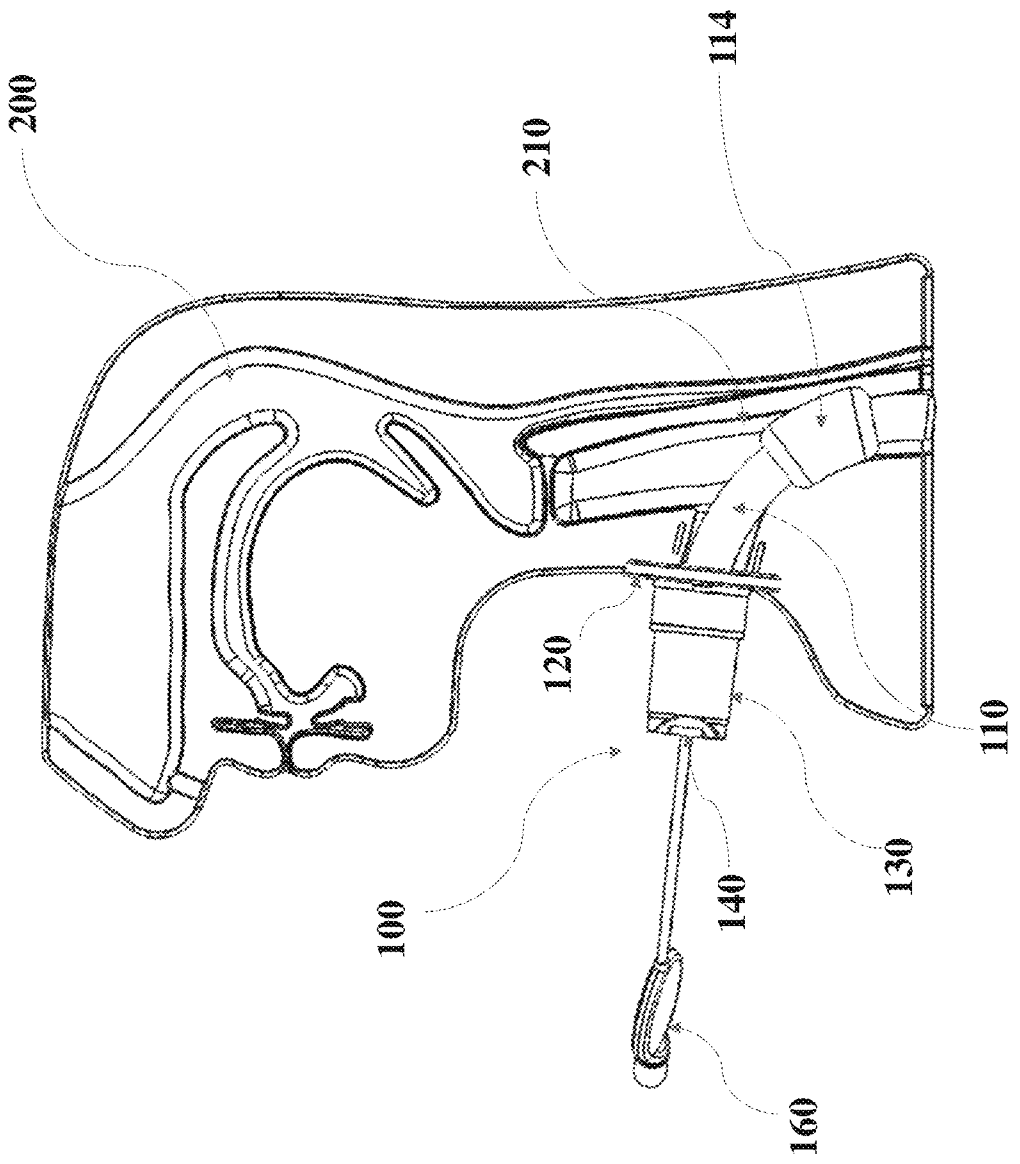
FIG. 1 illustrates an example tracheostomy tube assembly, a portion of which is inserted into a patient's trachea.

In the following detailed description, reference is made to the accompanying drawings, which form a part hereof. In the drawings, similar symbols typically identify similar components, unless context dictates otherwise. Thus, in some embodiments, part numbers may be used for similar components in multiple figures, or part numbers may vary from figure to figure. The illustrative embodiments described in the detailed description, drawings, and claims are not meant to be limiting. Some embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and made part of this disclosure.

Reference in the specification to "one embodiment," "an embodiment," or "in some embodiments" means that a particular feature, structure, or characteristic described in connection with the embodiment is included in at least one embodiment of the invention. Moreover, the appearance of these or similar phrases throughout the specification do not necessarily all refer to the same embodiment, nor are separate or alternative embodiments necessarily mutually exclusive. Various features are described herein which may be exhibited by some embodiments and not by others. Similarly, various requirements are described which may be requirements for some embodiments but may not be requirements for other embodiments.

Overview

A tracheostomy tube is an artificial airway inserted into the trachea of a patient to allow a more direct access for mechanical and non-mechanical ventilation. A tracheostomy tube assembly typically includes an outer cannula configured to be positioned in an airway of the patient, a flange member (or a "neckplate") secured about the outer cannula, an outer cannula connector (or a "hub") coupled to a proximal end of the outer cannula, and an inner cannula disposed inside the outer cannula and outer cannula connector. The inner cannula is removed for cleaning or replacement, such as when secretions or other contaminants build up. Also, if the inner cannula becomes fully or partially occluded with secretions or other matter, a patient may be unable to breathe through the inner cannula; thus, it is important that the inner cannula may be easily removed without disturbing the outer cannula and the patient's airway.

One difficulty that arises with tracheostomy tubes with an inner cannula is that the inner cannula should be removed without disturbing the outer cannula or without disturbing the placement of the tracheostomy tube on a patient. Excessive force on the tracheostomy tube, such as twisting or pulling motions, may cause decannulation of the tracheostomy tube, patient discomfort, harm the tissue surrounding the tracheostomy, or harm the patient's airway.

Some patients who are not on mechanical ventilation and are not able to tolerate a speaking valve may communicate by digitally (finger) occluding the tracheostomy tube. Digitally occluding the tube redirects the patient's exhaled air through the upper airway, vocal folds, mouth, and nose to restore communication. A difficulty that arises with some tracheostomy tubes with an inner cannula is that the face (or face portion) of the inner cannula may be shaped such that it is not possible or is difficult to digitally occlude the tracheostomy tube. For instance, some designs have two ears that protrude from the face of the inner cannula, which are compressed for removal of the inner cannula (see, e.g., FIG. 8 of U.S. Pat. No. 11,007,336). These designs allow for easy removal of the cannula but prevent a finger from sealing the inner cannula (due to the ears) to allow full airflow through the upper airway.

Accordingly, there is a need for improved tracheostomy tubes, and particularly for improved tracheostomy tubes that allow for easy placement and removal of the inner cannula. Also, there is a need to provide a tracheostomy tube that does not interfere with other devices connected to the hub and/or enables patients to digitally occlude the tracheostomy tube.

FIG. 1 illustrates an example tracheostomy tube assembly 100, a portion of which is inserted into a trachea 210 of a patient 200. The tracheostomy tube assembly 100 shown on FIG. 1 is merely an example, and the present disclosure is not limited thereto. For example, dimensions of the elements of the tracheostomy tube assembly 100 shown on FIG. 1 are merely example ones and other dimensions are also possible. Furthermore, shapes of the elements of the tracheostomy tube assembly 100 are merely examples and other shapes are also possible. Moreover, some elements may be optional and may be removed, and/or other elements may be added to the example tracheostomy tube assembly 100.

In the illustrated example, the tracheostomy tube assembly 100 includes an outer cannula 110, a flange 120, an outer cannula connector 130, and an inner cannula 140. The outer cannula 110 may be inserted into the trachea 210 of the patient 200 via a surgical incision or "stoma" in the neck of the patient 200. The outer cannula 110 may accommodate a head portion or proximal region of the inner cannula 140 therein. The outer cannula 110 may at least partially protect the inner cannula 140 from various body secretions of the patient when the tracheostomy tube assembly 100 is positioned in the patient. The tracheostomy tube assembly 100 may also include an pilot balloon 160 and a cuff 114 that are attached to the outer cannula 110 ("cuffed design"). The pilot balloon 160 may be used to inflate the cuff 114 to hold the outer cannula 110 in place within the trachea 210. The pilot balloon 160 may inflate along with the cuff 114 and serve as an indication of how much air pressure is in the cuff 114. The pilot balloon 160 may be used to inflate the cuff 114. The tracheostomy tube assembly 100 may not include a pilot balloon 160 and a cuff 114 ("cuffless design"). That is, the pilot balloon 160 and the cuff 114 may be optional elements.

The inner cannula 140 may be inserted into the outer cannula 110 via the outer cannula connector 130. The inner cannula 140 includes an opening 158 (not shown in FIG. 1; see FIG. 3C) to control the flow of air or other gases through the patient's trachea 210. The patient 200 may place his or her finger on the opening 158 to block the air flow into the patient's trachea from the outside (to be referred to as "finger occlusion," although it will be appreciated that the phrase includes occlusive devices other than a finger). The patient or a user (e.g., a caregiver or a healthcare professional) may release their finger from the opening 158 to unblock the air flow into the patient's trachea 210.

In some embodiments, the inner cannula 140 may include one or more grip protrusions (to be described in greater detail) for easy insertion into and removal from the outer cannula connector 130. For example, the patient 200 may grip the one or more grip protrusions with his or her finger when removing from and/or inserting into the outer cannula connector 130. The inner cannula 140 may be removed from the outer cannula 110 for cleaning, replacement, or other reasons. In some embodiments, the inner cannula 140 may include one or more mating protrusions (to be described in greater detail) on an outer wall thereof to be engaged with one or more mating recesses or one or more mating protrusions (to be described in greater detail) formed on an inner wall of the outer cannula connector 130 for easily and/or smoothly engaging with and removing from the outer cannula connector 130 with some friction.

The flange 120 may support the outer cannula 110 and the outer cannula connector 130. For example, the outer cannula connector 130 may extend from a front portion of the flange 120. A rear portion of the flange 120 may be placed on the neck of the patient when the outer cannula 110 is positioned inside the trachea 210 of the patient 200.

The outer cannula connector 130 receives the inner cannula 140 so that the inner cannula 140 is inserted into the outer cannula 110. The inner diameter of the outer cannula connector 130 may be similar to or slightly larger than the outer diameter of the largest portion of the inner cannula 140 so that a front portion (or a head portion) of the inner cannula 140 can be inserted into the outer cannula connector 130. The outer cannula connector 130 may comprise a material different from the inner cannula 140. For example, the inner cannula 140 comprises a flexible material whereas the outer cannula connector 130 comprises hard material such as plastic. The outer cannula connector 130 may be used for the patient to hold the outer cannula connector 130 (in addition to or in place of holding the flange 120) when the inner cannula 140 is inserted into or removed from the outer cannula connector 130.

In some embodiments, the outer cannula connector 130 may include one or more cutouts (to be described in more details) configured to expose the one or more grip protrusions of the inner cannula 140 when the inner cannula 140 is fully inserted into the outer cannula 110 through the outer cannula connector 130. As disclosed herein, "the inner cannula is fully inserted into the outer cannula" means that the inner cannula is properly installed in the outer cannula by fully inserting a portion (e.g., body) of the inner cannula into the outer cannula through the outer cannula connector. This does not mean that the entirety of the inner cannula is fully disposed within the outer cannula, but may generally mean that the body of the inner cannula is inserted into the outer cannula and the head portion of the inner cannula is inserted into the outer cannula connector. In some embodiments, each of the inner cannula 140 or the outer cannula connector 130 may include at least one of 1) one or more mating protrusions or 2) one or more mating recesses for smoothly engaging with and removing from each other with some friction.

Tracheostomy Tube Assembly (With Removed Inner Cannula)

Figure 2A:
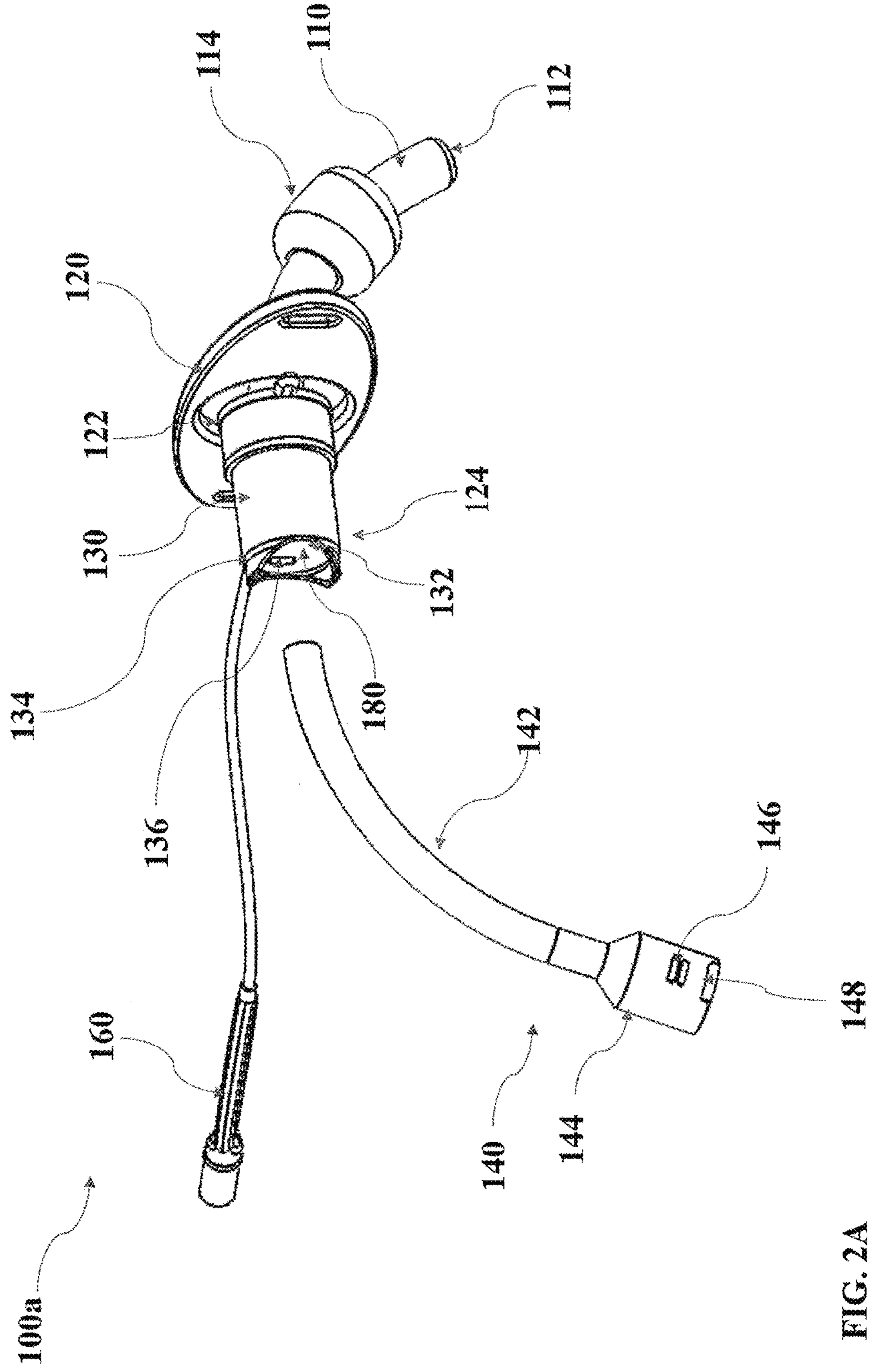
FIG. 2A is a perspective view of an example tracheostomy tube assembly in which an inner cannula has been fully removed from an outer cannula and outer cannula connector.
Figure 2B:
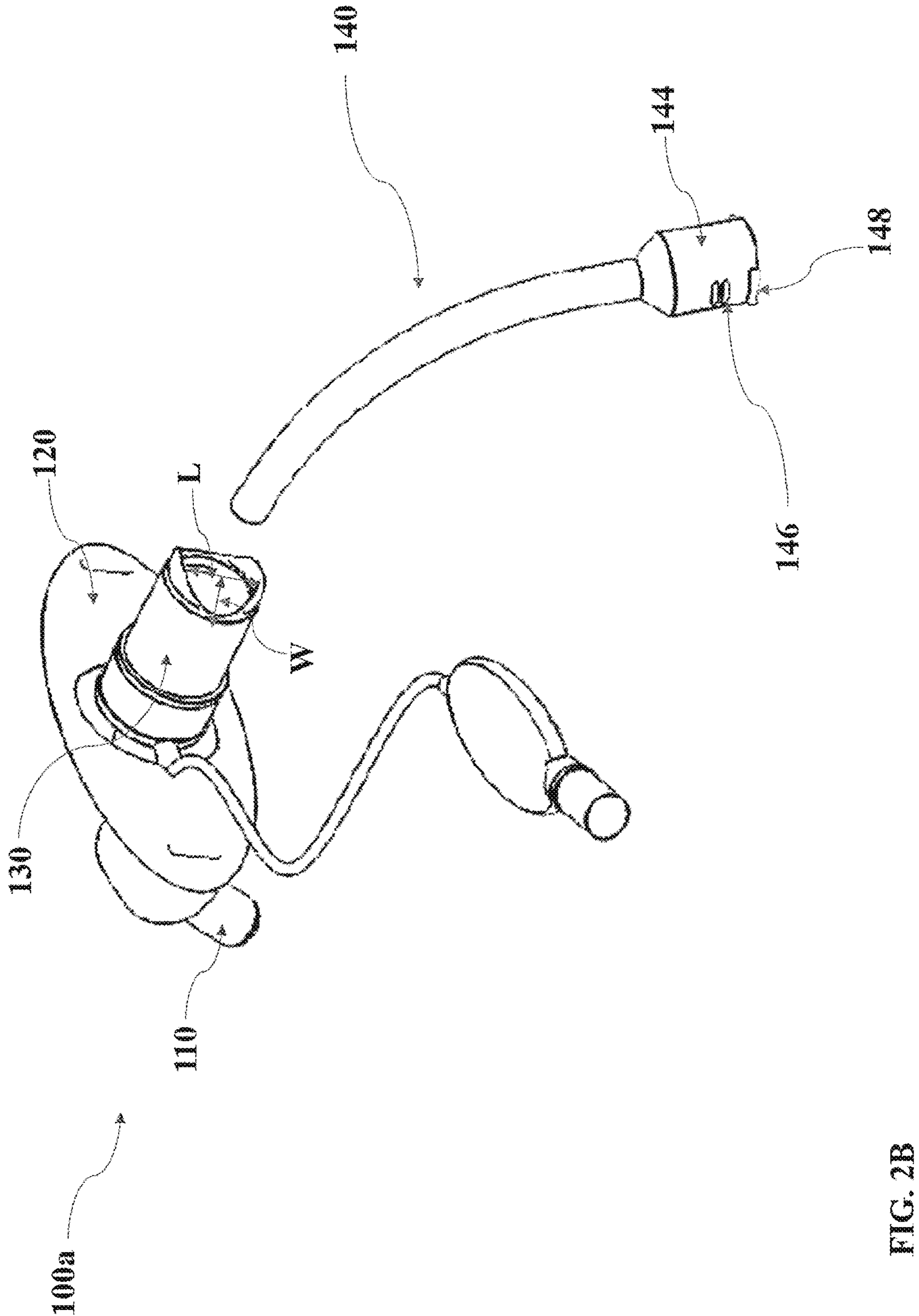
FIG. 2B is another perspective view of the example tracheostomy tube assembly of FIG. 2A.

FIG. 2A is a perspective view of an example tracheostomy tube assembly 100*a* in which an inner cannula 140 has been fully removed from an outer cannula 110 and an outer cannula connector 130. FIG. 2B is another perspective view of the example tracheostomy tube assembly 100*a*. The example tracheostomy tube assembly 100*a* may be substantially the same as or similar to the tracheostomy tube assembly 100 of FIG. 1.

The outer cannula connector 130 may include a distal region 122 coupled to the flange 120 and a proximal region 124 opposite to the distal region 122. As disclosed herein, the proximal region or proximal end may mean an area that is closer to a user of the tracheostomy tube assembly 100 than a distal region or a distal end. The outer cannula connector 130 may include one or more cutouts 132 that extend in a longitudinal direction of the outer cannula connector 130. The one or more cutouts 132 may be disposed or formed in the proximal region 124 of the outer cannula connector 130. The one or more cutouts 132 may be configured to expose one or more grip protrusions 148 formed on a proximal region (or head portion) 144 of the inner cannula 140, when the inner cannula 140 is fully inserted into the outer cannula 110. At least one of the one or more cutouts 132 may be sized to fully expose the one or more grip protrusions 148, when the inner cannula 140 is fully inserted into the outer cannula 110. In the illustrated example, the outer cannula connector 130 includes two cutouts 132. However, the present disclosure is not limited thereto. For example, a single cutout, or three or more cutouts may also be provided on the proximal region 124 of the outer cannula connector 130.

Referring to FIG. 2B, each of the one or more cutouts 132 incudes an opening distance (L) and a depth (W). The opening distance (L) may be between about 8 mm and about 15 mm (e.g., about 8 mm, about 9 mm, about 10 mm, about 11 mm, about 12 mm, about 13 mm, about 14 mm, about 15 mm, and ranges between such values). For example, the opening distance (L) may be between about 10 mm and about 12 mm.

The depth (W) may be between about 1 mm and about 8 mm (e.g., about 1 mm, about 2 mm, about 3 mm, about 4 mm, about 5 mm, about 6 mm, about 7 mm, about 8 mm, and ranges between such values). For example, the depth (W) may be between about 3 mm and about 6 mm.

The outer cannula connector 130 may also include a ridge 134. The ridge 134 may neighbor the one or more cutouts 132. The ridge 134 may be configured such that an outer end (or a face portion shown in FIG. 3A, 3C, 3E, or 3F) of the proximal region 144 of the inner cannula 140 rests upon the ridge 134. The ridge 134 may be tapered. For example, the ridge 134 may become gradually thinner in a direction extending from the proximal region 124 to the distal region 122 of the outer cannula connector 130. In some embodiments, the diameter of the ridge 134 may be about 15 mm or smaller to meet the current ISO standard (e.g., ISO Standard 5366). The outer cannula connector 130 may be tapered in a direction extending from the proximal region 124 to the distal region 122. In a non-limiting example, the diameter of the largest portion of the outer cannula connector 130 may be about 15 mm or smaller to meet the current ISO standard.

The outer cannula connector 130 may include one or more mating features on an inner wall thereof configured to interface with one or more mating features on an outer wall of the inner cannula 140. In a non-limiting example, the outer cannula connector 130 may include one or more mating recesses 136 formed on an inner wall thereof. The one or more mating recesses 136 may be engaged with the one or more mating protrusions formed on an outer wall of the inner cannula 140 when the inner cannula 140 is inserted into the outer cannula 110 via the outer cannula connector 130. For example, the one or more mating recesses 136 may be sized to respectively receive the one or more mating protrusions of the inner cannula 140 when the inner cannula 140 is inserted into the outer cannula 110. The one or more mating recesses 136 may include one or more first mating recesses 136 and one or more second mating recesses (not shown in FIG. 2A). The one or more second mating recesses may be disposed on an opposite side of the one or more first mating recesses 136. The number of the mating recesses described above are merely examples and the present disclosure is not limited thereto. For example, the one or more first recesses 136 may include three or more sets of mating recesses each set including one or more mating recesses.

Figure 3A:
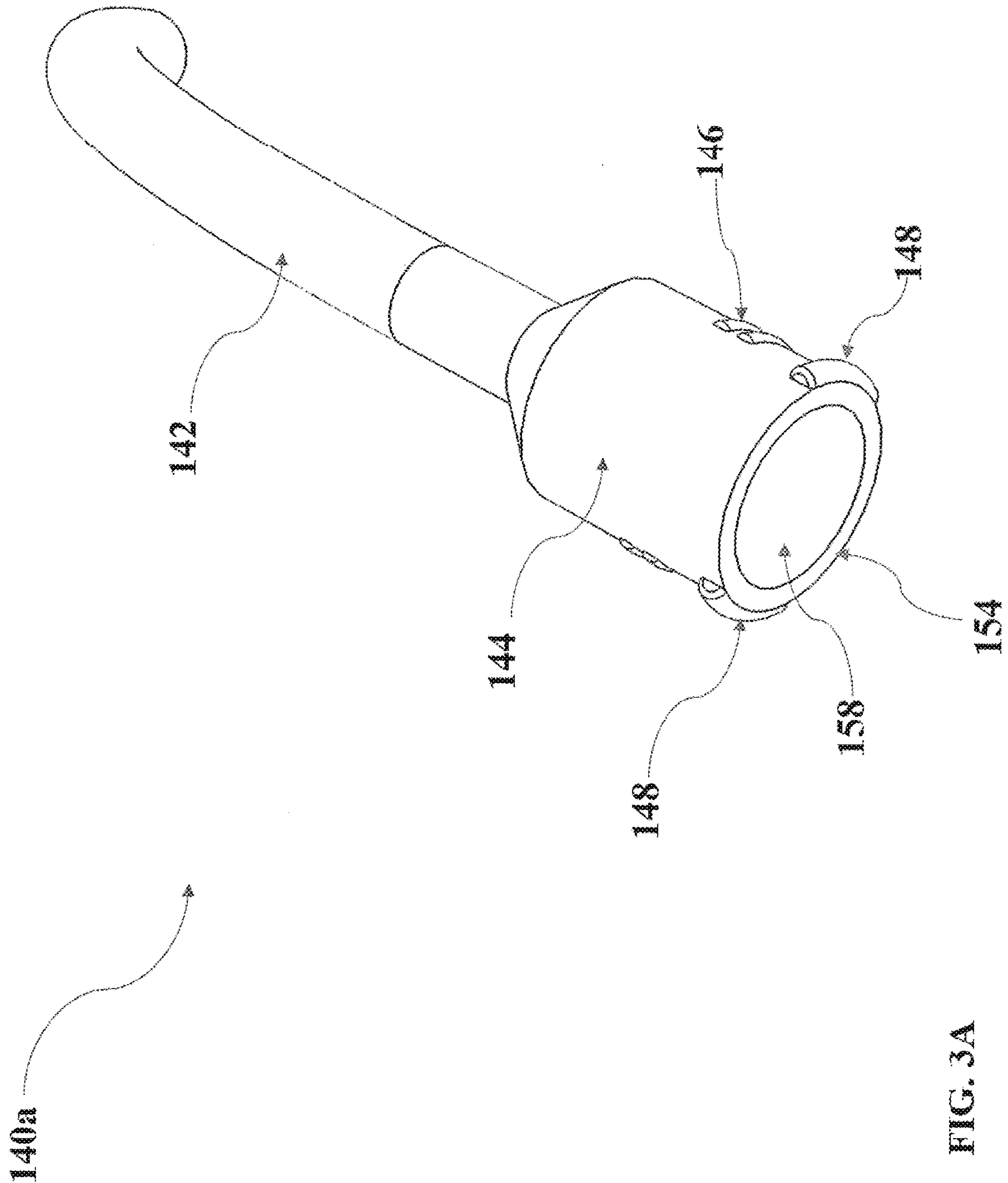
FIG. 3A is a perspective view of an example inner cannula.

In some embodiments, in addition to or in lieu of the one or more mating recesses 136, the outer cannula connector 130 may include one or more mating protrusions configured to be engaged with two or more mating protrusions of the inner cannula 140. In other words, the inner cannula 140 may include one or two or more mating protrusions 146 for each mating protrusion on the outer cannula connector 130. In a non-limiting example, the inner cannula 140 includes two mating protrusions 146 positioned parallel to each other along a length of the proximal region 144. As illustrated in FIG. 3A, the inner cannula 140 may include multiple sets of these mating protrusions 146 that are circumferentially spaced apart from each other around the proximal region 144. The outer cannula connector 130 may include one mating protrusion configured to be disposed between the two mating protrusions 146 of the inner cannula 140 so that the one mating protrusion of the outer cannula connector 130 may be latched between the two mating protrusions 146 of the inner cannula 140. In another non-limiting example, when the inner cannula 140 includes three mating protrusions, the outer cannula connector 130 may include two mating protrusions configured to be disposed between the three mating protrusions of the inner cannula 140 so that the two mating protrusions of the outer cannula connector 130 may be latched between the three mating protrusions of the inner cannula 140. In some embodiments, when the two mating protrusions of the outer cannula connector 130 include first and second mating protrusions, and the three mating protrusions of the inner cannula 140 include first, second, and third mating protrusions, the first mating protrusion of the outer cannula connector 130 may be latched between the first and second mating protrusions of the inner cannula 140. Similarly, the second mating protrusion of the outer cannula connector 130 may be latched between the second and third mating protrusions of the inner cannula 140.

In some embodiments, the outer cannula connector 130 may include one or more mating protrusions instead of the one or more mating recesses. In these embodiments, the inner cannula 140 may include one or more mating recesses. The one or more mating protrusions of the outer cannula connector 130 may be engaged with the one or more mating recesses of the inner cannula 140. In the above embodiments, the outer cannula connector 130 may include the same number of the one or more mating protrusions as that of the one or more mating recesses of the inner cannula 140.

In some embodiments, neither of the outer cannula connector 130 and the inner cannula may include one or more mating protrusions or recesses. In these embodiments, the outer diameter of the inner cannula 140 may be slightly larger than the inner cannula example that includes one or more mating protrusions to provide some friction against the inner wall of the outer cannula connector 130.

In the illustrated example, the one or more mating recesses 136 of the outer cannula connector 130 are disposed not to overlap the ridge 134 in a longitudinal direction of the outer cannula connector 130. However, the present disclosure is not limited thereto. For example, the one or more mating recesses 136 and/or additional one or more mating protrusions or recesses may be disposed to overlap the ridge 134 in a longitudinal direction of the outer cannula connector 130.

Each of the one or more mating recesses 136 includes a length ($L_{mr}$), a width ($W_{mr}$), and a height or depth ($H_{mr}$) ($L_{mr}$, $W_{mr}$, and $H_{mr}$ not labeled in the drawings). The length ($L_{mr}$) may be between about 1 mm and about 8 mm (e.g., about 1 mm, about 2 mm, about 3 mm, about 4 mm, about 5 mm, about 6 mm, about 7 mm, about 8 mm, and ranges between such values). For example, the length ($L_{mr}$) may be between about 3 mm and 5 mm. The width ($W_{mr}$) may be between about 0.5 mm and about 4 mm (e.g., about 0.5 mm, about 1 mm, about 1.5 mm, about 2 mm, about 2.5 mm, about 3 mm, about 3.5 mm, about 4 mm, and ranges between such values). For example, the width ($W_{mr}$) may be between about 1 mm and 2.5 mm. The height ($H_{mr}$) may be between about 0.5 mm and about 3.5 mm (e.g., about 0.5 mm, about 1 mm, about 1.5 mm, about 2 mm, about 2.5 mm, about 3 mm, about 3.5 mm, and ranges between such values). For example, the height ($H_{mr}$) may be between about 1 mm and 2 mm. When the outer cannula connector 130 includes one or more mating protrusions, the dimensions of at least one of the one or more mating protrusions of the outer cannula connector 130 may be the same as those of the one or more mating recesses 136 described above.

The inner cannula 140 may include a head portion or proximal region 144 and a body 142. At least a portion of the body may be referred to as a distal region. At least part of the proximal region 144 may be exposed by the outer cannula connector 130 when inserted into the outer cannula 110 via a connector opening 180 (see FIG. 2A) of the outer cannula connector 130. In some embodiments, the body 142 of the inner cannula 140 may have a length to be fully accommodated in the outer cannula 110 so that no portion of the body 142 protrudes from an inner end 112 of the outer cannula 110. In some embodiments, the body 142 of the inner cannula 140 may have a length to protrude from the inner end 112 of the outer cannula 110. The proximal region 144 may be larger in diameter or width than the body 142 so that the body 142 can be easily inserted into the outer cannula 110 while the proximal region 144 can be engaged with the inner wall of the outer cannula connector 130.

In some embodiments, the inner cannula 140 may include one or more grip protrusions 148 that allow for a patient or user to grip with their finger when removing the inner cannula 140 from and/or inserting the inner cannula 140 into the outer cannula connector 130. The one or more grip protrusions 148 may be fully exposed by the one or more cutouts 132 when the inner cannula 140 is fully inserted into the outer cannula 110. At least one of the one or more grip protrusions 148 may be tapered in a direction toward the body 142. In a non-limiting example, the diameter of the largest portion of the inner cannula 140 may be about 15 mm or smaller to meet the current ISO standard. This can facilitate removal and insertion of the inner cannula 140 by hand while preventing interference with various devices (e.g., speaking valve, occlusion adapter, etc.) that can be connected to the outer cannula connector 130.

In the illustrated examples, the inner cannula 140 includes two sets of a single grip protrusion or first grip protrusion 148 (see FIG. 2A and FIG. 2B) that are disposed on opposite sides of the proximal region 144 of the inner cannula 140. However, the present disclosure is not limited thereto. In a non-limiting example, each grip protrusion set may include two or more grip protrusions. In these embodiments, the two or more grip protrusions may be sized to be fully accommodated in the cutouts 132 of the outer canula connector 130. In another non-limiting example, the grip protrusion sets may include different numbers of grip protrusions. For example, one grip protrusion set may include two or more grip protrusions, and another grip protrusion set may include a single grip protrusion, or three or more grip protrusions. In these embodiments, the two or more grip protrusions, or the three or more grip protrusions may be sized to be fully accommodated in the cutouts 132 of the outer canula connector 130. In some embodiments, each grip protrusion set may include at least one grip protrusion having a size different from that of another grip protrusion of the other grip protrusion set. As illustrated, the inner cannula **140*a* includes a pair of grip protrusions 148 projecting radially outward of a body of the proximal region 144. The pair of grip protrusions 150 are diametrically opposed from each other. The grip protrusions 150 may project radially outward relative to the mating protrusions 146. The grip protrusions 150 may extend a greater distance around a circumference of the proximal region 144 compared to the mating protrusions 146. Each grip protrusion 148 extends from the face portion 154 of the inner cannula 140. Each grip portion 148** may be arcuate in shape.

Each of the one or more grip protrusions 148 includes a length ($L_{gp}$), a width ($W_{gp}$), and a height ($H_{gp}$) ($L_{gp}$, $W_{gp}$, and $H_{gp}$ not labeled in the drawings). The length ($L_{gp}$) may be between about 4 mm and about 10 mm (e.g., about 4 mm, about 5 mm, about 6 mm, about 7 mm, about 8 mm, about 9 mm, about 10 mm, and ranges between such values). For example, the length ($L_{gp}$) may be between about 6.5 mm and about 8 mm. The width ($W_{gp}$) may be between about 0.5 mm and about 4 mm (e.g., about 0.5 mm, about 1 mm, about 1.5 mm, about 2 mm, about 2.5 mm, about 3 mm, about 3.5 mm, about 4 mm, and ranges between such values). For example, the width ($W_{gp}$) may be between about 1 mm and about 2.5 mm. The height ($H_{gp}$) may be between about 0.5 mm and about 3.5 mm (e.g., about 0.5 mm, about 1 mm, about 1.5 mm, about 2 mm, about 2.5 mm, about 3 mm, about 3.5 mm, and ranges between such values). For example, the height ($H_{gp}$) may be between about 1 mm and about 2 mm.

In some embodiments, the inner cannula 140 may include one or more mating protrusions 146 formed on an outer wall of the proximal region 144. In some embodiments, the one or more mating protrusions 146 may be engaged with the one or more mating recesses 136 formed on the inner wall of the outer cannula connector 130. The one or more mating protrusions 146 may be engaged with one or more mating protrusions formed on the inner wall of the outer cannula connector 130.

In some embodiments where the outer cannula connector 130 may include one or more mating protrusions, the inner cannula 140 may include one or more mating recesses configured to be engaged with the one or more mating protrusions of the outer cannula connector 130.

In some embodiments where the outer cannula connector 130 may include one or more mating protrusions and one or more mating recesses, the inner cannula 140 may include one or more mating recesses configured to be engaged with the one or more mating protrusions of the outer cannula connector 130 and one or more mating protrusions configured to be engaged with the one or more mating recesses of the outer cannula connector 130.

Each of the one or more mating protrusions 146 includes a length ($L_{mp}$), a width ($W_{mp}$), and a height ($H_{mp}$) ($L_{mp}$, $W_{mp}$, and $H_{mp}$ not labeled in the drawings). The length ($L_{mp}$) may be between about 1 mm and about 8 mm (e.g., about 1 mm, about 2 mm, about 3 mm, about 4 mm, about 5 mm, about 6 mm, about 7 mm, about 8 mm, and ranges between such values). For example, the length ($L_{mp}$) may be between about 3 mm and 5 mm. The width ($W_{mp}$) may be between about 0.5 mm and about 4 mm (e.g., about 0.5 mm, about 1 mm, about 1.5 mm, about 2 mm, about 2.5 mm, about 3 mm, about 3.5 mm, about 4 mm, and ranges between such values). For example, the width ($W_{mp}$p) may be between about 1 mm and 2.5 mm. The height ($H_{mp}$) may be between about 0.5 mm and about 3.5 mm (e.g., about 0.5 mm, about 1 mm, about 1.5 mm, about 2 mm, about 2.5 mm, about 3 mm, about 3.5 mm, and ranges between such values). For example, the height ($H_{mp}$) may be between about 1 mm and 2 mm.

The above dimensions for the cutouts 132, the mating recesses (and/or mating protrusions) 136, the grip protrusions 148, and the mating protrusions (and/or mating recesses) 146 are merely example ones and the present disclosure is not limited thereto. In some embodiments, the dimensions of at least one of the mating protrusion, mating recess, or grip protrusion may be larger or smaller than the above described ranges. For example, each of the above dimensions may be larger or smaller by about 0.5%, about 1%, about 5%, about 10%, about 20%, about 30%, about 40%, about 50% of the corresponding dimensions, or any number therebetween. When the dimension of one element becomes smaller or lager, the dimensions of the other elements may become proportionally smaller or larger.

The inner cannula 140 may be made from various materials, e.g., including, but not limited to, polytetrafluoroethylene (PTFE), low-density polyethylene (LDPE), high-density polyethylene (HDPE), polyvinyl chloride (PVC), or polymethylpentene (PMP). The outer cannula connector 130 may be made from various materials, e.g., including, but not limited to, polytetrafluoroethylene (PTFE), low-density polyethylene (LDPE), high-density polyethylene (HDPE), polyvinyl chloride (PVC), polymethylpentene (PMP), or silicone rubber. The outer cannula 110 may be made from various materials, e.g., including, but not limited to polytetrafluoroethylene (PTFE), low-density polyethylene (LDPE), high-density polyethylene (HDPE), polyvinyl chloride (PVC), polymethylpentene (PMP), or silicone rubber.

The mating recesses 136 or mating protrusions of the outer cannula connector 130 may be formed using the same manufacturing process (e.g., molding) as the outer cannula connector 130. For example, the mating recesses 136 or mating protrusions of the outer cannula connector 130 may be integrally formed with the remaining part of the outer cannula connector 130. The mating protrusions 146 of the inner cannula 140 may be formed using the same manufacturing process (e.g., molding) as the inner cannula 140. For example, the mating protrusions 146 or mating recesses of the inner cannula 140 may be integrally formed with the remaining part of the inner cannula 140. The grip protrusion 148 of the inner cannula 140 may be formed using the same manufacturing process (e.g., molding) as the inner cannula 140. For example, the grip protrusion 148 may be integrally formed with the remaining part of the proximal region of the inner cannula 140.

Figure 2C:
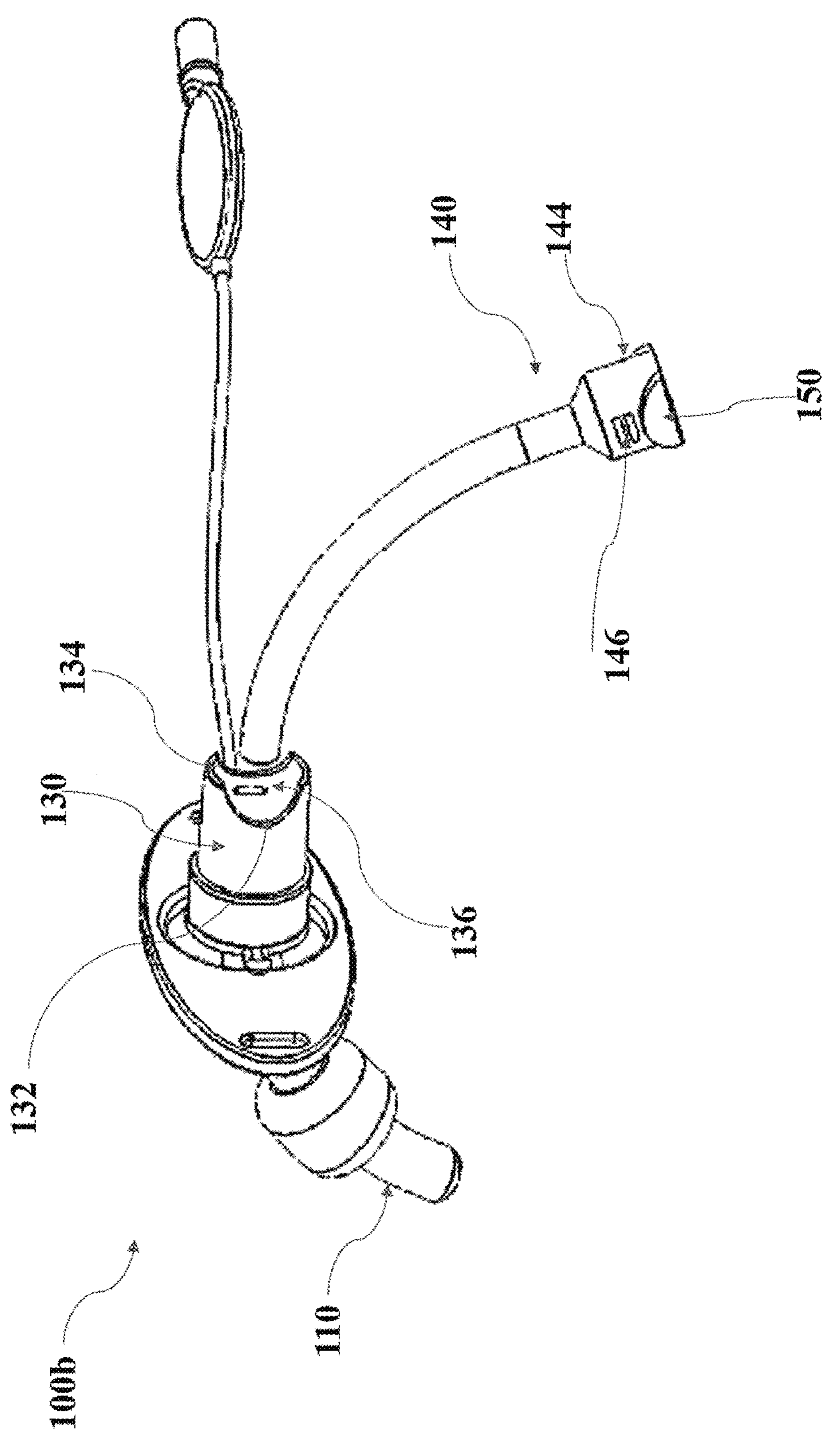
FIG. 2C is a perspective view of another example tracheostomy tube assembly in which an inner cannula has been fully removed from an outer cannula and outer cannula connector.
Figure 2D:
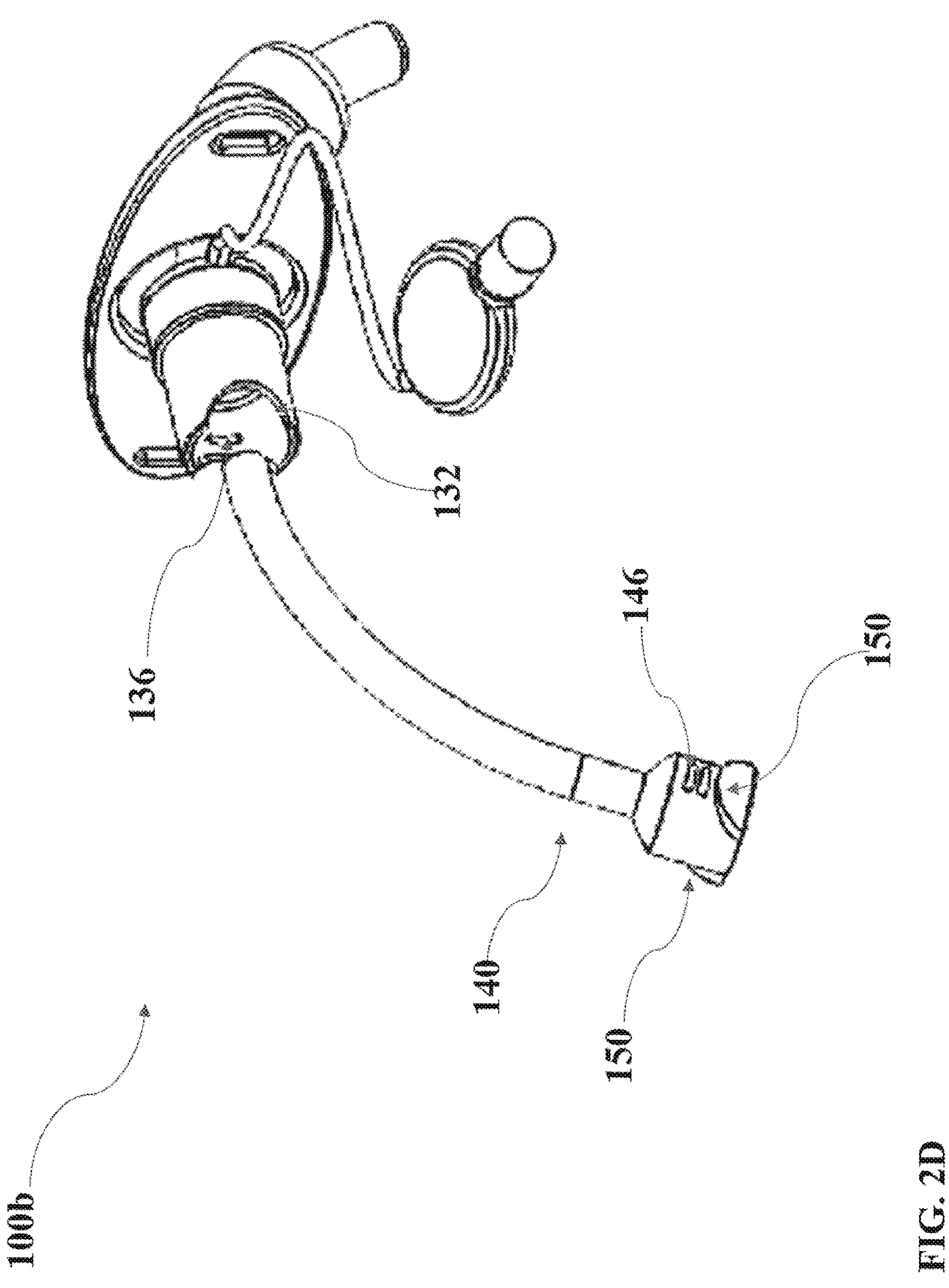
FIG. 2D is another perspective view of the example tracheostomy tube assembly of FIG. 2C.

FIG. 2C is a perspective view of another example tracheostomy tube assembly 100*b* in which an inner cannula 140 has been fully removed from an outer cannula 110 and an outer cannula connector 130. FIG. 2D is another perspective view of the example tracheostomy tube assembly 100*b* of FIG. 2C. The example tracheostomy tube assembly 100*b* of FIGS. 2C and 2D is substantially the same as or similar to the example tracheostomy tube assembly 100*a* of FIGS. 2A and 2B except that in the example tracheostomy tube assembly 100*b* of FIGS. 2C and 2D, the inner cannula 140 may include a second grip protrusion 150 (or grip protrusion 150) that is larger than the first grip protrusion 148 (grip protrusion 148) of the example tracheostomy tube assembly 100*a* of FIGS. 2A and 2B. The grip protrusion 150 may be substantially fully accommodated in the cutout 132 of the outer cannula connector 130. For example, the grip protrusion 150 may have the same dimension as, substantially the same dimension as, or a dimension similar to that of the cutout 132 of the outer cannula connector 130. In these embodiments, the grip protrusion 150 may be fully or substantially fully accommodated in the cutout 132. The grip protrusion 150 may be flush or substantially flush with an outer wall of the outer cannula connector 130 that is adjacent to the grip protrusion 150 when the inner cannula 140 is fully inserted into the outer cannula 110. In some embodiments, the grip protrusion 150 may be lower than the outer wall of the outer cannula connector 130. In some embodiments, the grip protrusion 150 may have a dimension slightly less than that of the cutout 132. In these embodiments, the grip protrusion 150 may be fully accommodated in the cutout 132. The grip protrusion 150 may be formed by the same manufacturing process (e.g., molding) used for manufacturing the inner cannula 140. For example, the grip protrusion 150 may be integrally formed with the remaining part of the proximal region of the inner cannula 140. At least one of the one or more grip protrusions 150 may be tapered in a direction toward the body 142. In a non-limiting example, the diameter of the largest portion (e.g., the grip protrusion 150) of the inner cannula 140 may be about 15 mm or smaller to meet the current ISO standard. This can facilitate removal and insertion of the inner cannula 140 by hand while preventing interference with various devices that can be connected to the outer cannula connector 130.

Inner Cannula

Figure 3B:
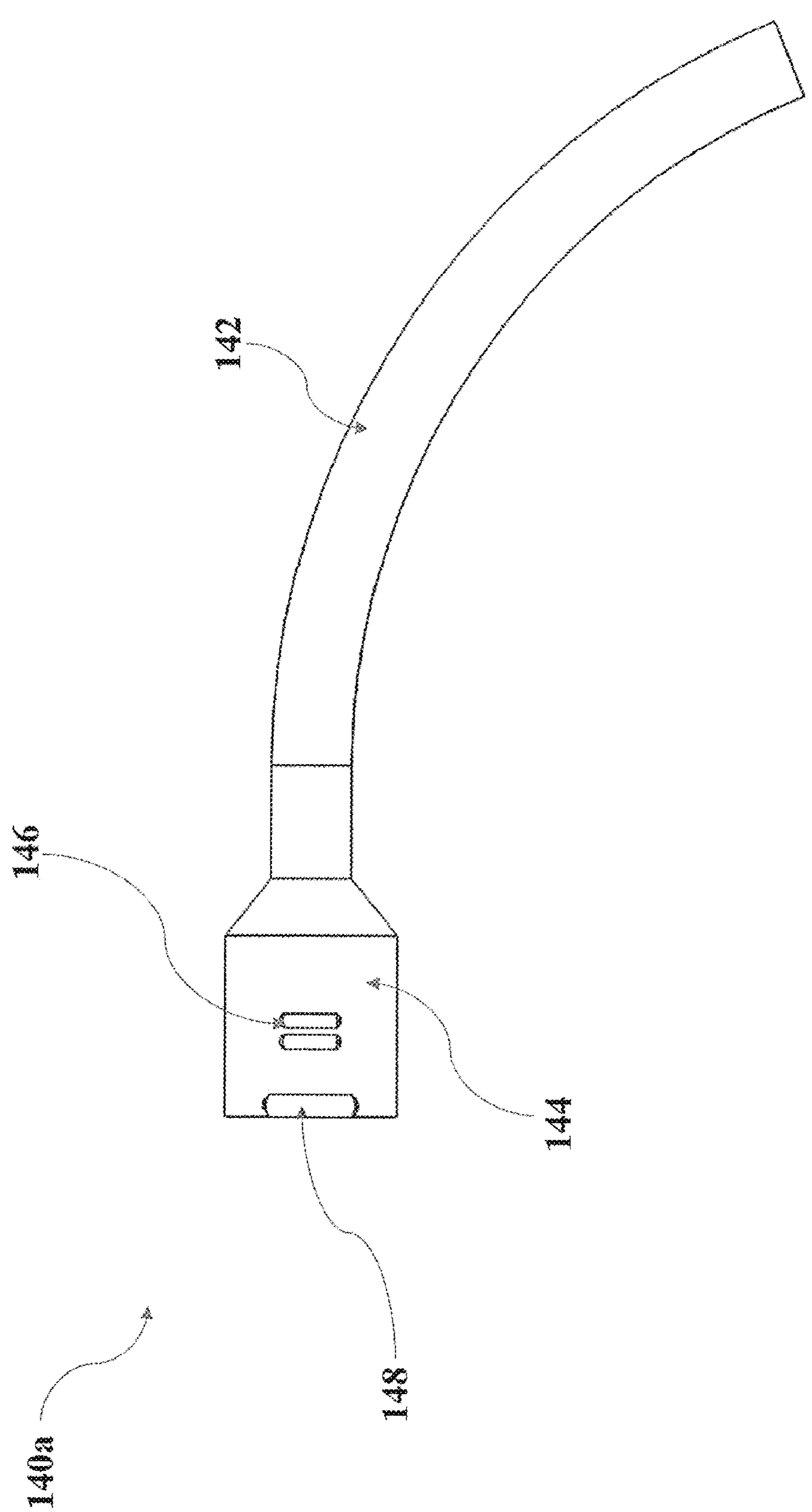
FIG. 3B is a side view of the example inner cannula of FIG. 3A.

FIG. 3A is a perspective view of an example inner cannula 140*a*. FIG. 3B is a side view of the example inner cannula 140*a* of FIG. 3A. The example inner cannula 140*a* may be substantially the same as or similar to the inner cannula 140 of FIG. 1.

The inner cannula 140*a* may be used with the tracheostomy tube assembly 100*a* shown in FIGS. 2A and 2B. The inner cannula 140*a* may include a head portion or proximal region 144 and a body 142. The proximal region 144 may include one or more grip protrusions 148, and one or more sets of mating protrusions 146, and a face portion 154. At least one of the grip protrusions 148, the mating protrusions 146, or the face portion 154 may be integrally formed with the remaining portion of the proximal region 144 or the inner cannula 140.

In the illustrated example, the proximal region 144 includes two grip protrusions 148. The two grip protrusions 148 may be disposed on opposite sides of the proximal region 144. However, the present disclosure is not limited thereto. For example, the proximal region 144 may include one grip protrusion, or three or more grip protrusions disposed in different locations of the proximal region 144. As another example, each grip protrusion set may include two or more grip protrusions disposed in two or more locations of the proximal region 144. As another example, one grip protrusion set may include a single grip protrusion, and another grip protrusion set may include two or more grip protrusions.

At least one of the grip protrusions 148 may be flush with an outer surface of the outer cannula connector 130 that is adjacent to the grip protrusions 148 when the inner cannula 140 is fully inserted into the outer cannula 110. However, the present disclosure is not limited thereto. For example, at least one of the grip protrusions 148 may not be flush with an outer surface of the outer cannula connector adjacent to the grip protrusions 148 when the inner cannula 140 is fully inserted into the outer cannula 110. In this example, at least one of the grip protrusions 148 may be lower in height than the outer surface of the outer cannula connector 130 when the inner cannula 140 is fully inserted into the outer cannula 110.

At least one of the one or more grip protrusions 148 may be tapered in a direction toward the body 142. In a non-limiting example, the diameter of the largest portion (e.g., the grip protrusion 148) of the inner cannula 140*a* may be about 15 mm or smaller to meet the current ISO standard. This can facilitate removal and insertion of the inner cannula 140 by hand while preventing interference with various devices that can be connected to the outer cannula connector 130.

The proximal region 144 may include an opening 158 for a user to finger occlude the tracheostomy tube assembly 100*a*, or occlude the tracheostomy tube assembly 100*a* with the use of an occlusion adapter that may be configured to cover the opening 158 and part of the proximal region 144. The opening 158 may be sized to be fully covered by a finger of an average adult.

In some embodiments, the proximal region 144 may be tapered in a direction toward the body 142. In some embodiments, the proximal region 144 may not be tapered. In these examples, the outer diameter of the proximal region 144 may not be larger than 15 mm according to the current ISO standard so that the proximal region may fit in the outer cannula connector 130. The face portion 154 may be larger in diameter than an outer diameter of the outer cannula connector 130 so that a user may grip the face portion 154 when inserting into and removing from the outer cannula connector 130. In a non-limiting example, the diameter of the face portion 154 may be 15 mm or less to meet the current ISO standard.

Figure 3C:
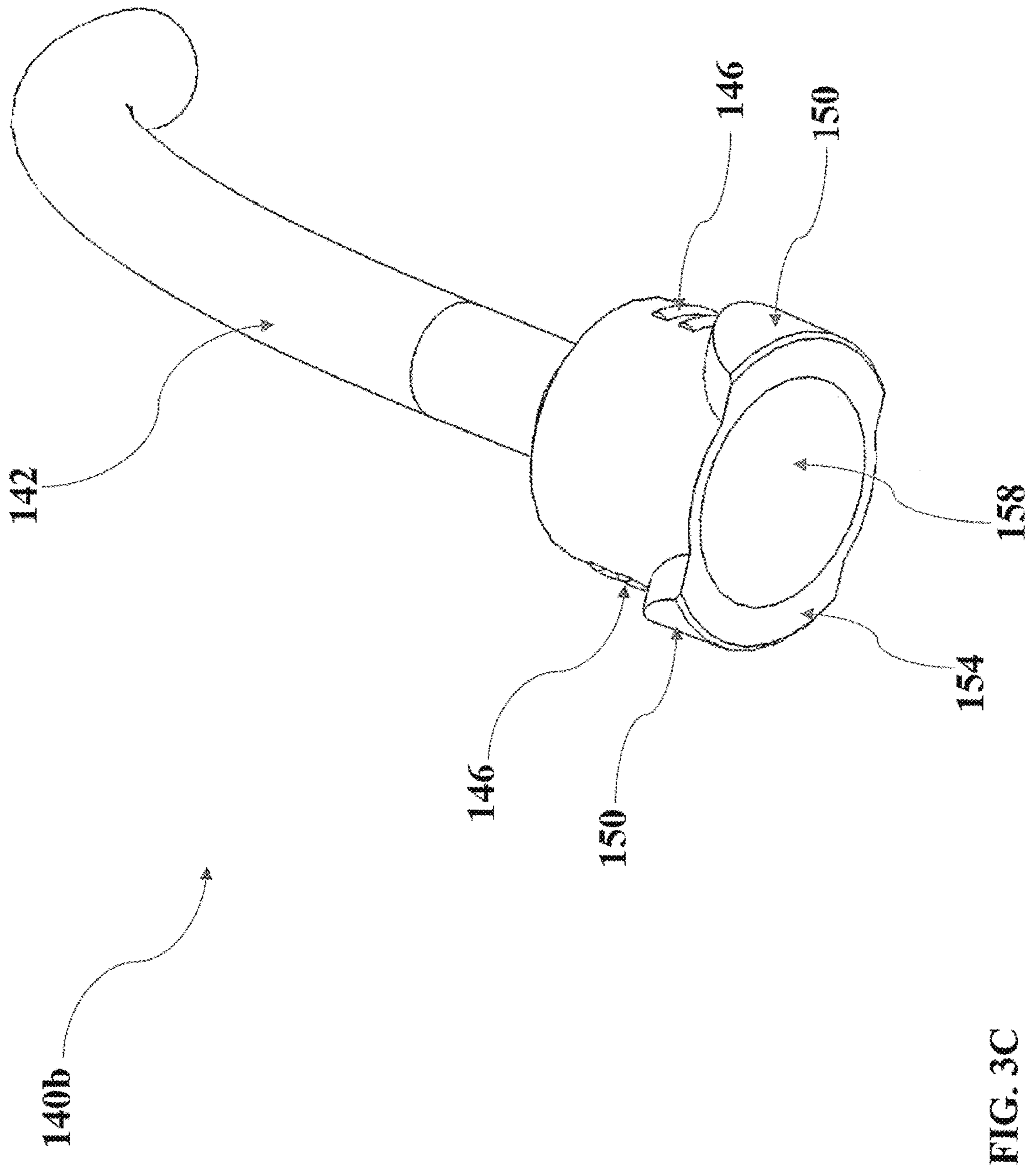
FIG. 3C is a perspective view of another example inner cannula.
Figure 3D:
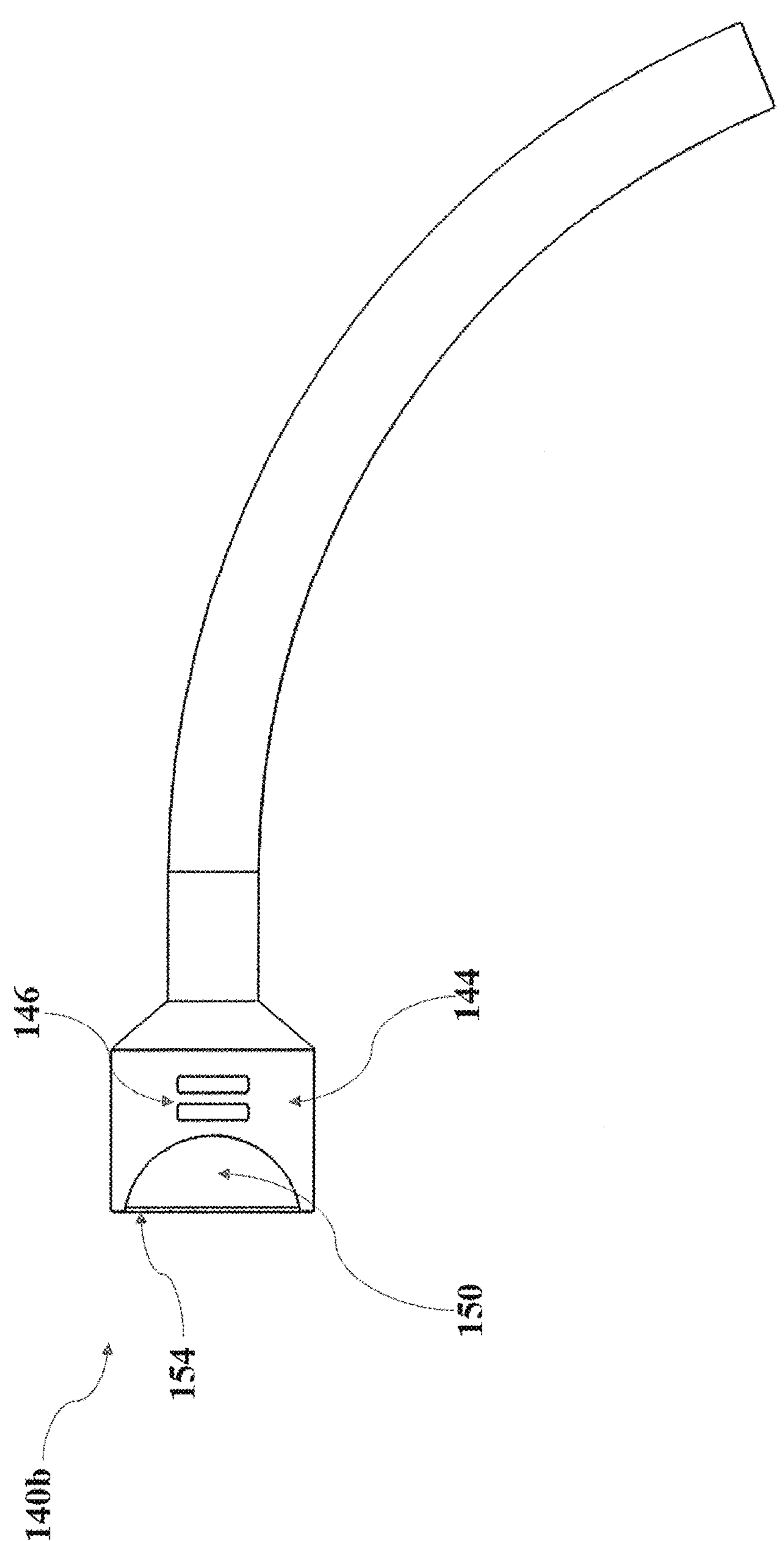
FIG. 3D is a side view of the example inner cannula of FIG. 3C.

FIG. 3C is a perspective view of another example inner cannula 140*b*. FIG. 3D is a side view of the example inner cannula 140*b* of FIG. 3C. The example inner cannula 140*b* of FIGS. 3C and 3D is substantially the same as the example inner cannula 140*a* of FIGS. 3A and 3B except that the example inner cannula 140*b* of FIGS. 3C and 3D includes a grip protrusion 150 larger than the grip protrusion 148 shown in FIGS. 3A and 3B. In some embodiments, the grip protrusion 150 may have the same dimension or substantially the same dimension as that of the cutout 132 of the outer cannula connector 130. In these embodiments, the grip protrusion 150 may be fully or substantially fully accommodated in the cutout 132 when the inner cannula 130 is inserted into the outer cannula 110. As illustrated, the inner cannula 140*b* includes a pair of grip protrusions 150 projecting radially outward of a body of the proximal region 144. The pair of grip protrusions 150 are diametrically opposed from each other. The grip protrusions 150 may project radially outward relative to the mating protrusions 146. Each grip protrusion 150 extends from the face portion 154 of the inner cannula 140. Each grip portion 150 may be semi-circular in shape.

In a non-limiting example, the grip protrusion 150 may be flush or substantially flush with a portion of the outer cannula connector 130 that is adjacent to the cutout 132 when the inner cannula 140 is fully inserted into the outer cannula 110. In another non-limiting example, the grip protrusion 150 may not be flush with the portion of the outer cannula connector 130 that is adjacent to the cutout 132 when the inner cannula 140 is fully inserted into the outer cannula 110. In this example, the grip protrusion 150 may be lower in height than the portion of the outer cannula connector 130 that is adjacent to the cutout 132 when the inner cannula 140 is fully inserted into the outer cannula 110. In some embodiments, the grip protrusion 150 may have a dimension slightly less than that of the cutout 132. In these embodiments, the grip protrusion 150 may be fully accommodated in the cutout 132. In the examples shown in FIGS. 3A-3D, a user may grab at least one of the grip protrusion (148/150) or the face portion 154 when inserting the inner cannula 140 into the outer cannula 110 or removing the inner cannula 140 from the outer cannula 110.

Figure 3E:
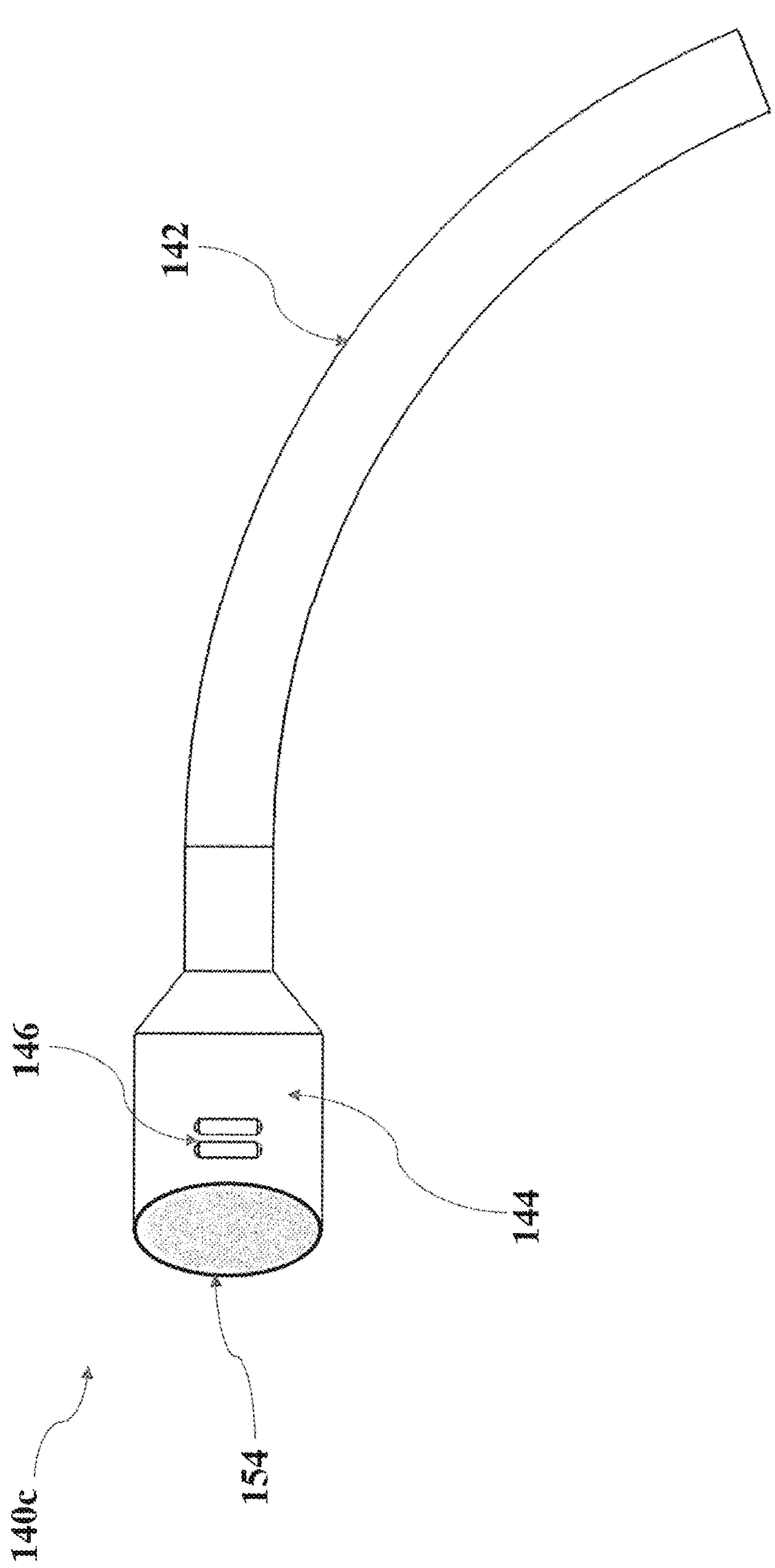
FIG. 3E is a side view of another example inner cannula.

FIG. 3E is a side view of another example inner cannula 140*c*. The example inner cannula 140*c* of FIG. 3E is substantially the same as or similar to the example inner cannula 140*a* of FIGS. 3A and 3B, except that the example inner cannula 140*c* of FIG. 3E does not include a grip protrusion. In some embodiments, the outer cannula connector 130 may not include a cutout.

The inner cannula 140*c* may include a face portion 154. The face portion 154 may be exposed by the outer cannula connector 130 when the inner cannula 140*c* is inserted into the outer cannula 110. As described above, the diameter of the face portion 154 may be larger than at least a portion of the outer cannula connector 130 that immediately neighbors the face portion 154, when the inner cannula 140 is inserted into the outer cannula 110. Thus, the face portion 154 may allow for a user to grip when inserting the inner cannula 140*c* into or remove the inner cannula 140*c* from the outer cannula 110, even when no grip protrusion (such as 148 or 150) is provided on the proximal region 144 of the inner cannula 140.

In some embodiments, the face portion 154 may be made through the same manufacturing process as the inner cannula 140*c*. In a non-limiting example, the inner cannula 140*c* may be made by a molding process, and the face portion 154 may be made by the same molding process. The face portion 154 may be integrally formed with the proximal region 144 of the inner cannula 140*c*.

Figure 3F:
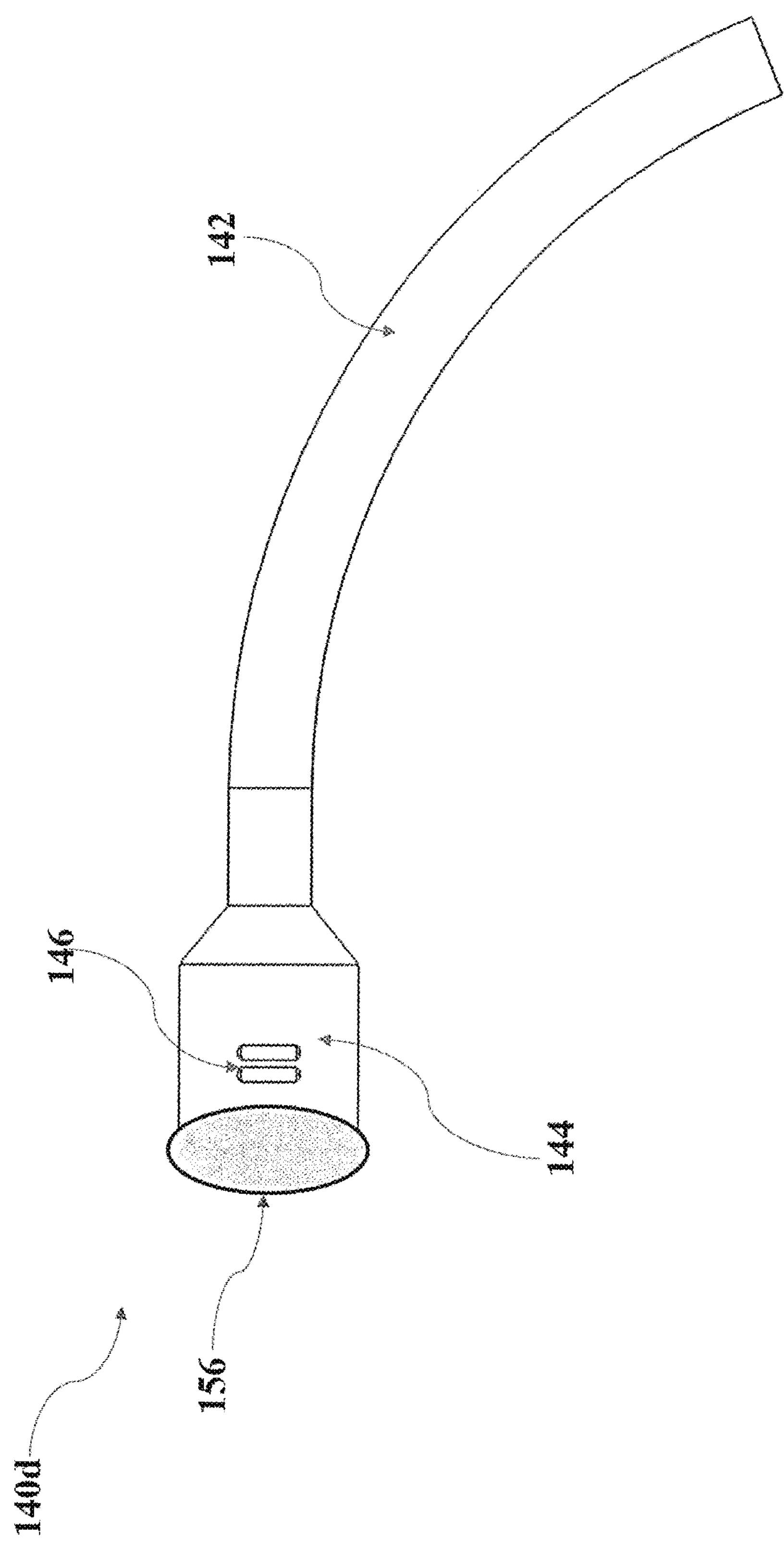
FIGS. 3F-3J are side views of another example inner cannulas.

FIG. 3F is a side view of another example inner cannula 140*d*. The example inner cannula 140*d* of FIG. 3F is substantially the same as or similar to the example inner cannula 140*c* of FIG. 3E, except that the example inner cannula 140*d* of FIG. 3F includes a larger face portion 156 compared to the smaller face portion 154 of the example inner cannula 140*c* of FIG. 3E. Similar to FIG. 3E, in this example, the outer cannula connector 130 may not include a cutout.

In a non-limiting example, the face portion 156 may have a diameter of 15 mm or less to meet the current ISO standard. In this example, the outer diameter of the proximal region 144 of the inner cannula 140*d* shown in FIG. 3F may be smaller than the outer diameter of the proximal region 144 of the inner cannula 140*c* of FIG. 3E due to the larger face portion 156.

In a non-limiting example, the face portion 1556 may be larger than the face portion 154 by about 5% to about 20%. The face portion 156 may be exposed by the outer cannula connector 130 when the inner cannula 140*d* is inserted into the outer cannula 110. In this example, the face portion 156 may allow for a user to grip when inserting the inner cannula 140*d* into or remove the inner cannula 140*d* from the outer cannula 110.

Similarly to the face portion 154, the face portion 156 may be made through the same manufacturing process as the inner cannula 140*d*. In a non-limiting example, the inner cannula 140*d* may be made by a molding process, and the face portion 156 may be made by the same molding process. The face portion 156 may be integrally formed with the proximal region 144 of the inner cannula 140*d*. The face portion 156 may be made from the same material as the remaining portion of the inner cannula 140*d* including that of the proximal region 144.

Tracheostomy Tube Assembly (With Inserted Inner Cannula)

Figure 4A:
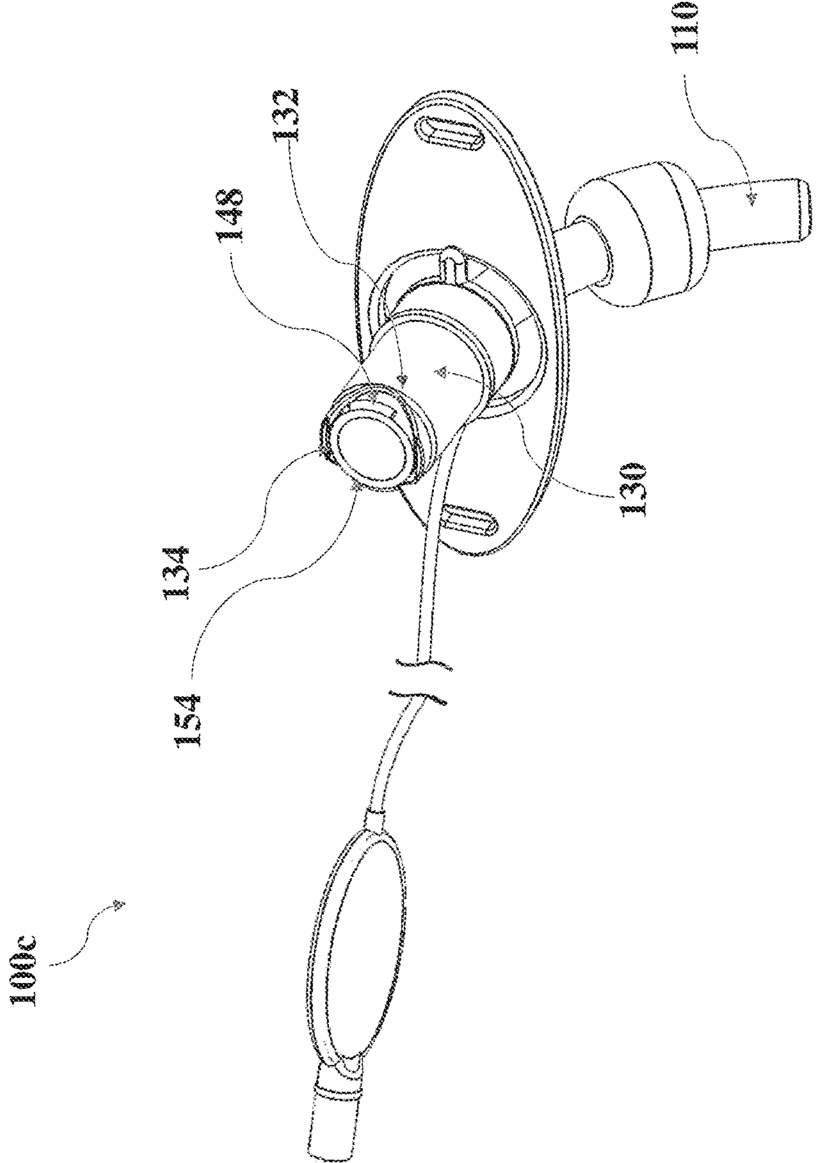
FIG. 4A is a perspective view of an example tracheostomy tube assembly in which an inner cannula has been fully inserted into an outer cannula through an outer cannula connector.
Figure 4B:
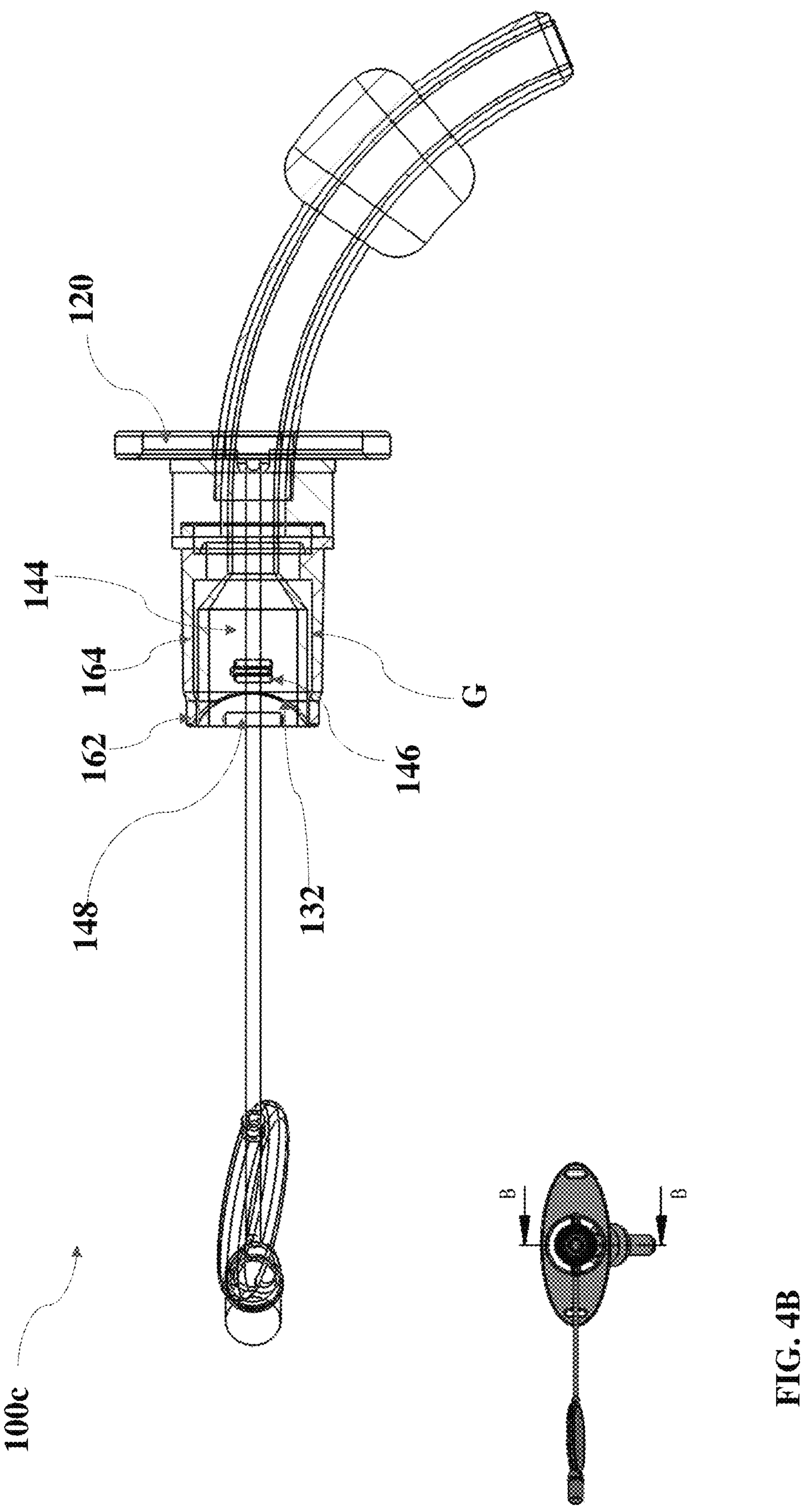
FIG. 4B is a side view of the example tracheostomy tube assembly of FIG. 4A.
Figure 4C:
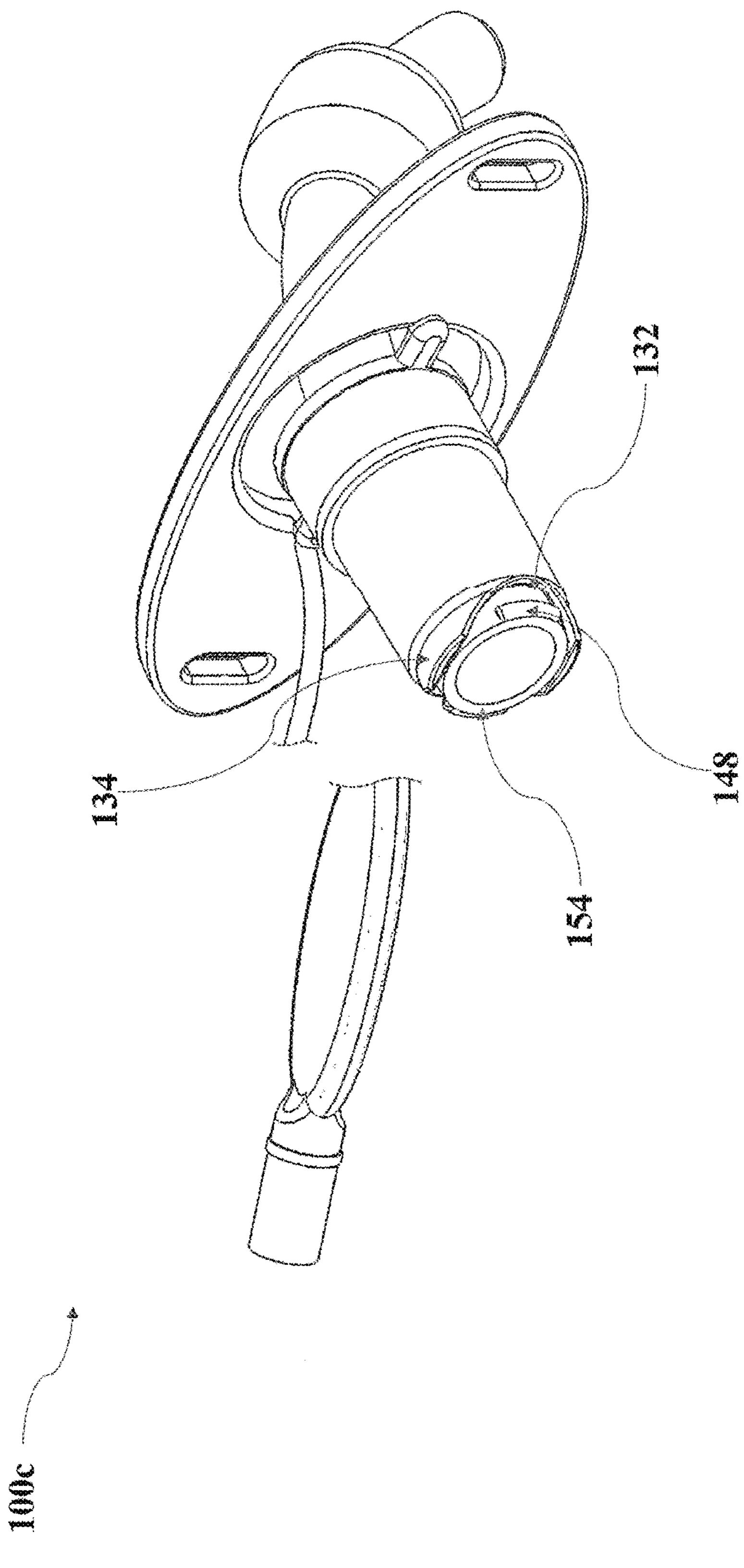
FIG. 4C is a magnified view of an outer cannula connector of the tracheostomy tube assembly of FIG. 4A.
Figure 4D:
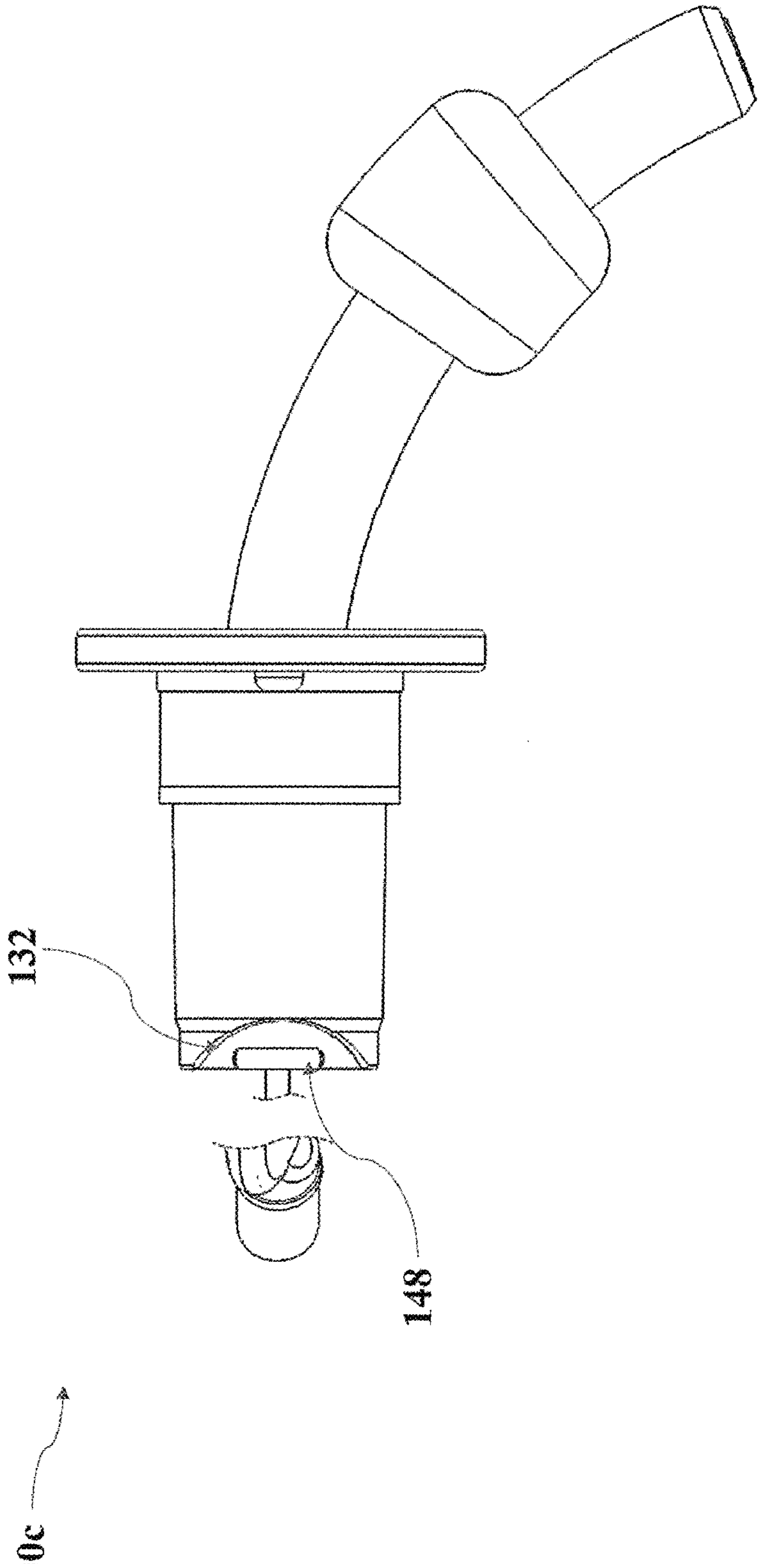
FIG. 4D is another side view of the tracheostomy tube assembly of FIG. 4A.

FIG. 4A is a perspective view of an example tracheostomy tube assembly 100*c* in which an inner cannula (not labeled in FIG. 4A) has been fully inserted into an outer cannula 110 through an outer cannula connector 130. FIG. 4B is a side view of the example tracheostomy tube assembly 100*c* of FIG. 4A. FIG. 4C is a magnified view of the outer cannula connector 130 of the tracheostomy tube assembly 100*c* of FIG. 4A. FIG. 4D is another side view of the tracheostomy tube assembly 100*c* of FIG. 4A. The example tracheostomy tube assembly 100*c* of FIG. 4A may be substantially the same as or similar to the example tracheostomy tube assembly 100*a* of FIG. 2A.

Referring to FIG. 4A, FIG. 4C, and FIG. 4D, the grip protrusion 148 is exposed by the cutout 132 when the inner cannula is fully inserted into the outer cannula 110 through the outer cannula connector 130, so that a user can easily hold the grip protrusion 148 when they try to remove the inner cannula from the outer cannula 110, or insert the inner cannula into the outer cannula 110.

Figure 3G:
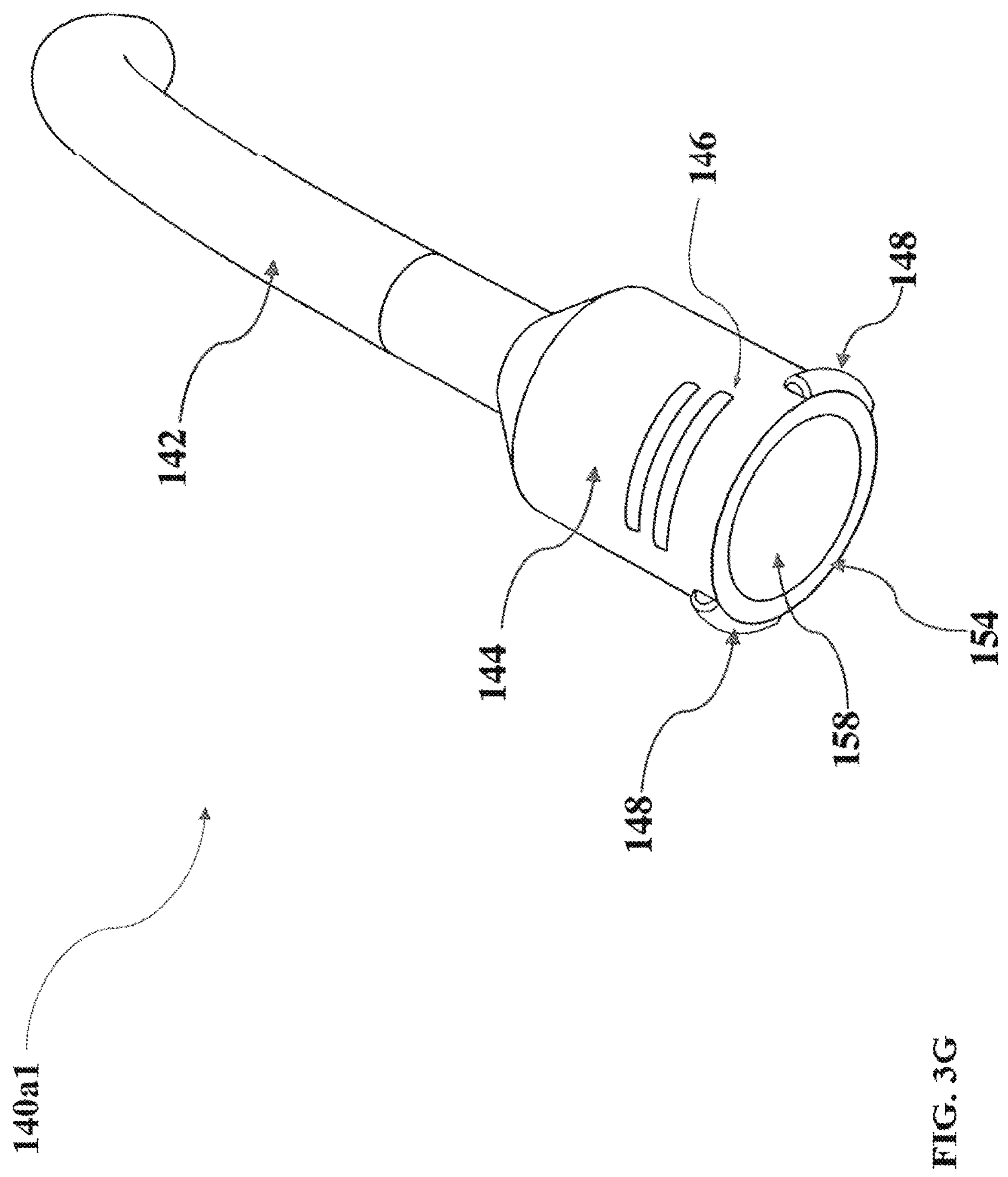
Figure 3H:
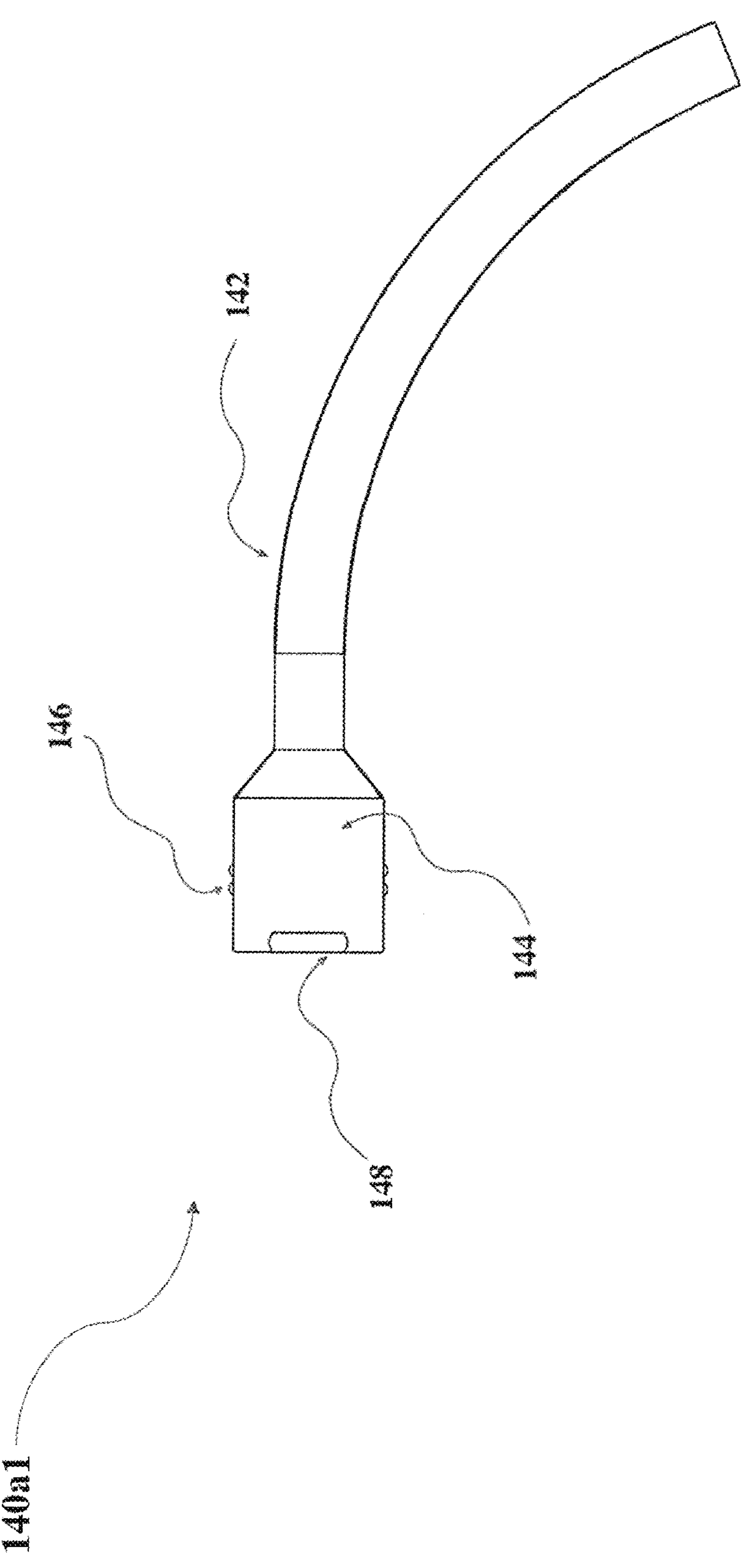
Figure 3I:
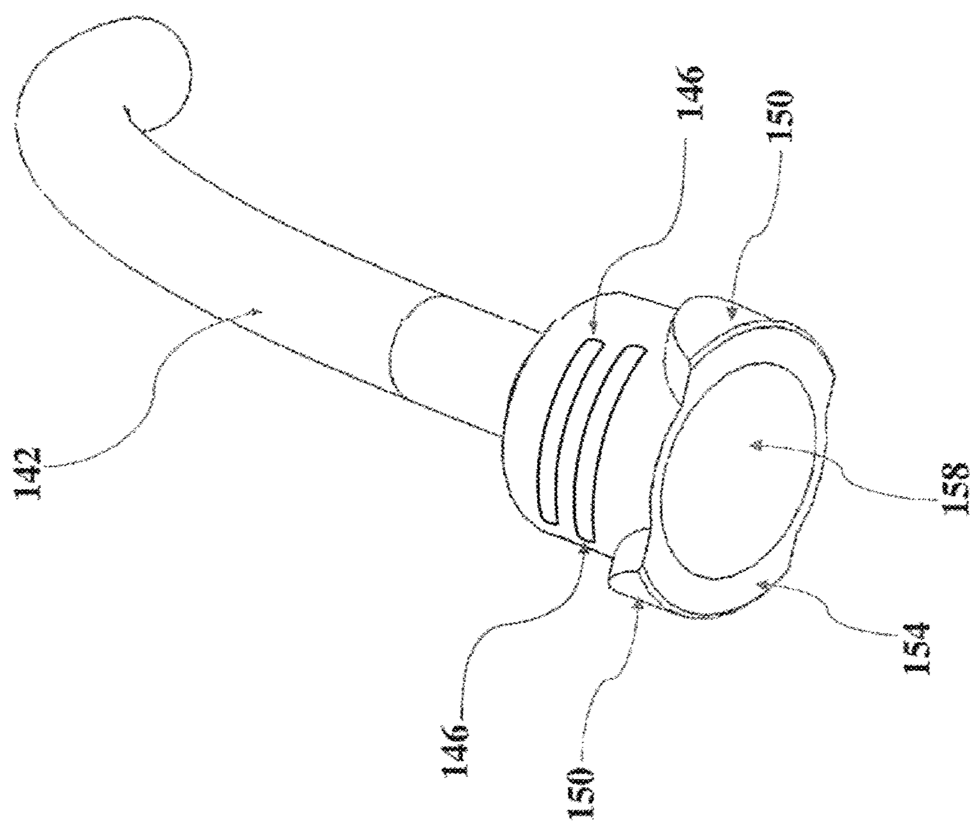
Figure 3I:
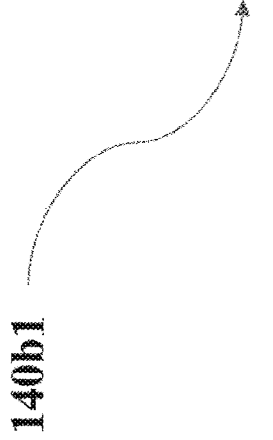
Figure 3J:
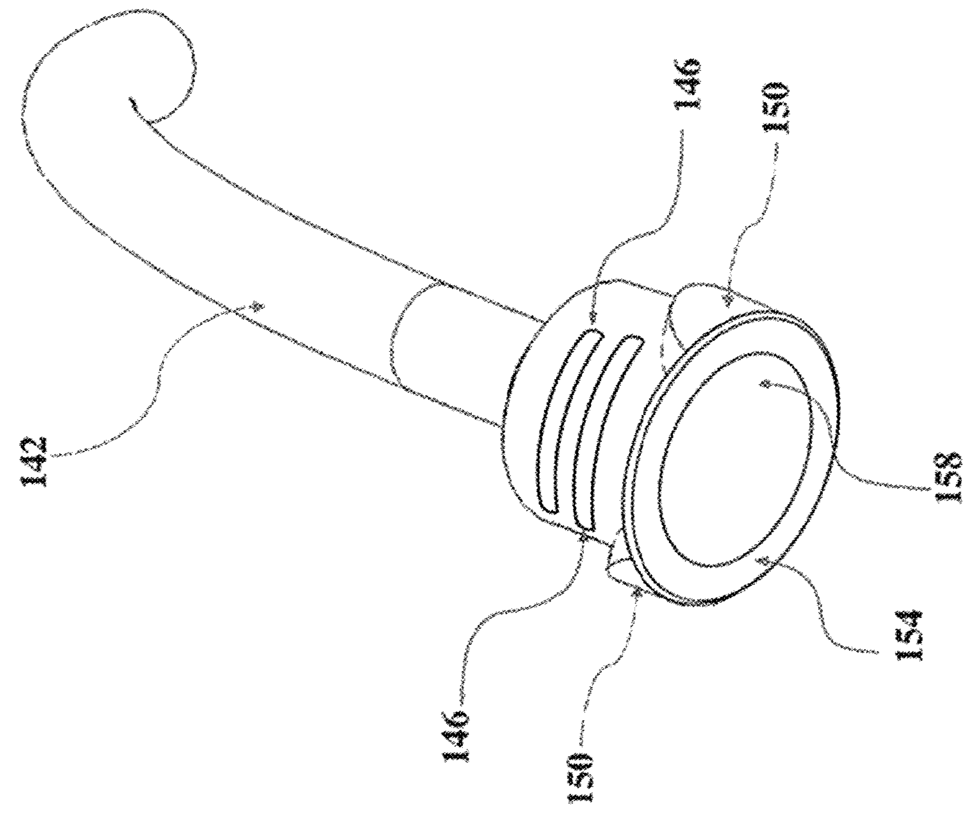
Figure 3J:
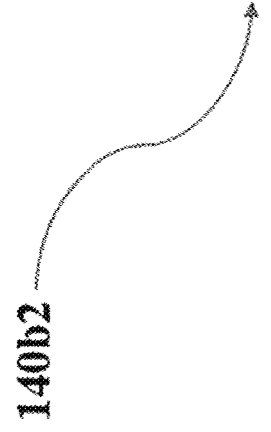
Figure 4E:
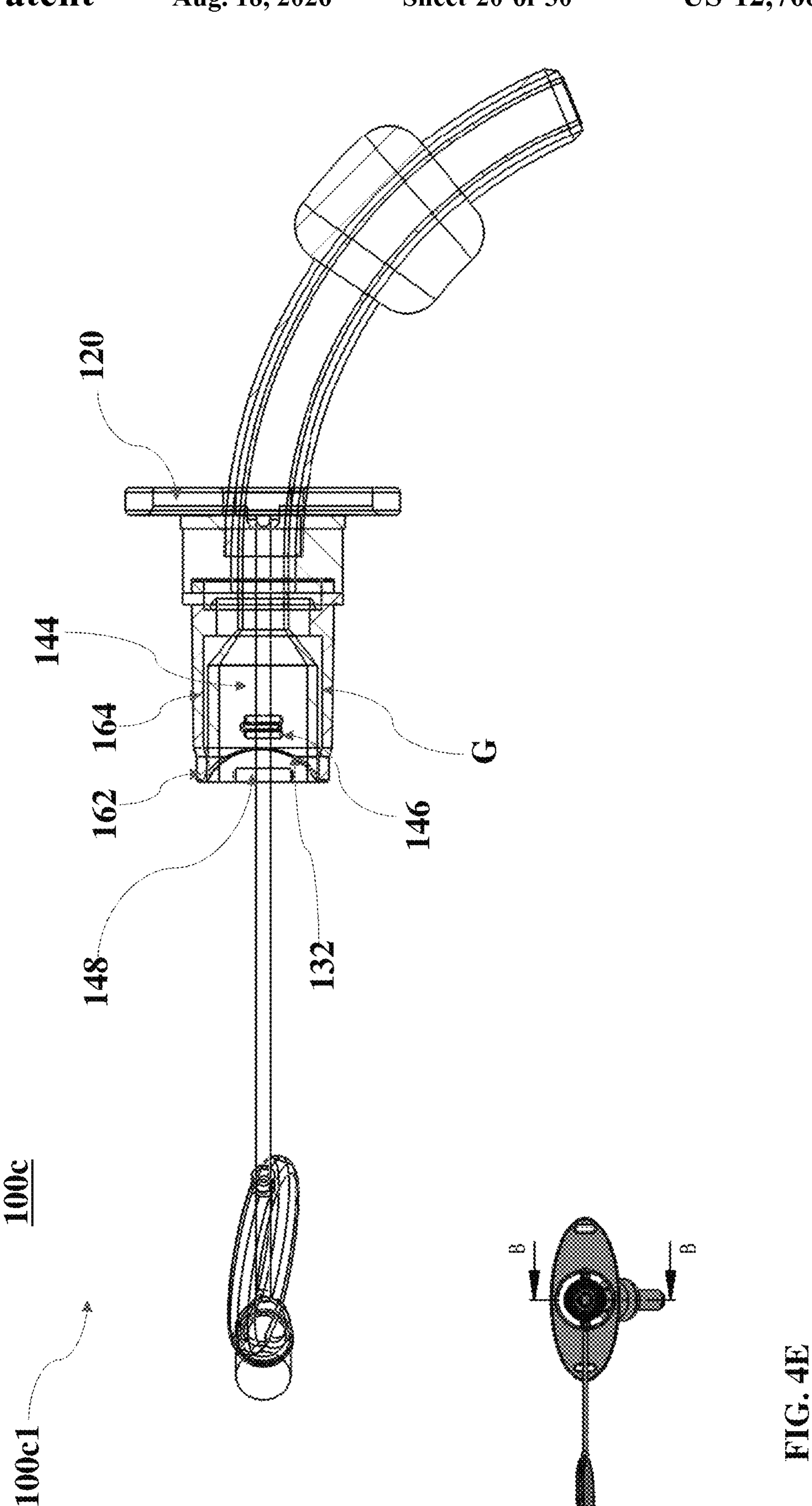
FIG. 4E is a side view of another tracheostomy tube assembly.

In some embodiments, as shown in FIG. 4B, the mating protrusions 146 of the inner cannula are engaged with the mating recesses or mating protrusions of the outer cannula connector 130. In the illustrated example, the mating protrusions/recesses are disposed to be aligned with the grip protrusion 148 in a longitudinal direction of the outer cannula connector 130. However, the present disclosure is not limited thereto. For example, in addition to or in place of the mating protrusions 146 (or recesses), additional mating protrusions and/or recesses may be formed in other positions that may not overlap the grip protrusion in the longitudinal direction (see, for example, reference numeral 140*al* in FIGS. 3G and 3H, reference numeral 140*b*1 in FIG. 3I, reference numeral 140*b*2 in FIG. 3J, reference numeral 100*c*1 in FIG. 4E, reference numeral 100*d*1 in FIG. 5D, and reference numeral 100*d*2 in FIG. 5E). The proximal region 144 of the inner cannula may be tapered toward the flange 120. For example, the width or diameter of the proximal region may gradually become smaller from a left end thereof to a right end thereof that is closer to the flange 120 than the left end. This tapered structure may facilitate insertion of the inner cannula into the outer cannula connector 130 or removal of the inner cannula 140 from the outer cannula connector 130 due to a less friction between the tapered outer wall of the inner cannula and the inner wall of the outer cannula connector 130.

In some embodiments, an outer wall of the proximal region 144 of the inner cannula may not be tapered. In these embodiments, the inner wall of the outer cannula connector 130 may be tapered in an opposite direction (i.e., the inner wall becomes wider from a left end to a right end. In some embodiments, the outer wall of the proximal region 144 of the inner cannula may be tapered in a direction, and the inner wall of the outer cannula connector 130 may be tapered in an opposite direction. In the above embodiments where at least one of the outer wall of the proximal region 144 or the inner wall of the outer cannula connector 130 is tapered, a first portion 162 of the outer cannula connector 130 may contact an outer wall of the proximal region 144 and a second portion 164 of the outer cannula connector 130 may not contact an outer wall of the proximal region 144. There may be a gap (G) formed (in the second portion 164) between the outer wall of the proximal region 144 and the inner wall of the outer cannula connector 130 (see FIG. 4B).

Figure 5A:
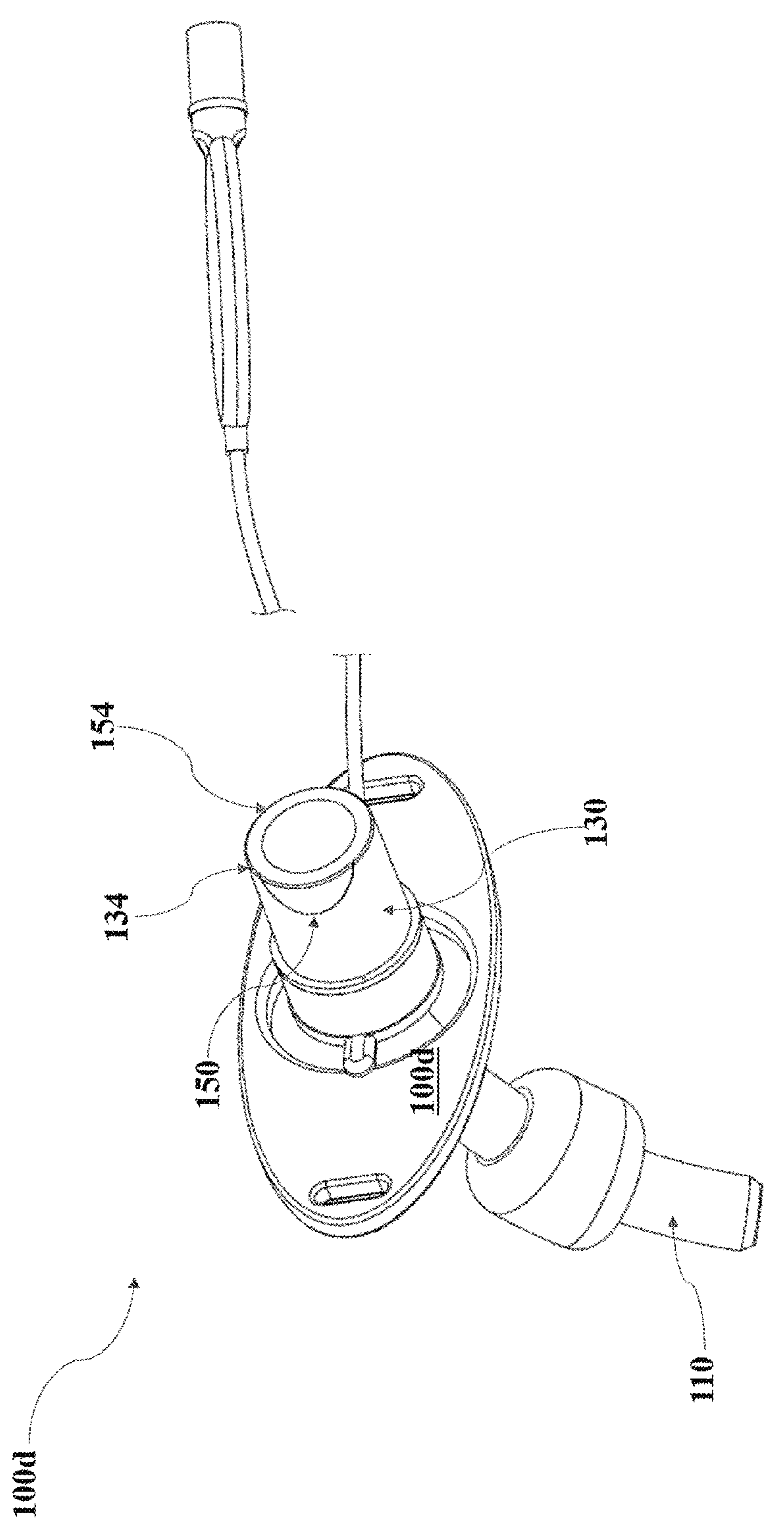
FIG. 5A is a perspective view of another example tracheostomy tube assembly in which an inner cannula has been fully inserted into an outer cannula via an outer cannula connector.
Figure 5B:
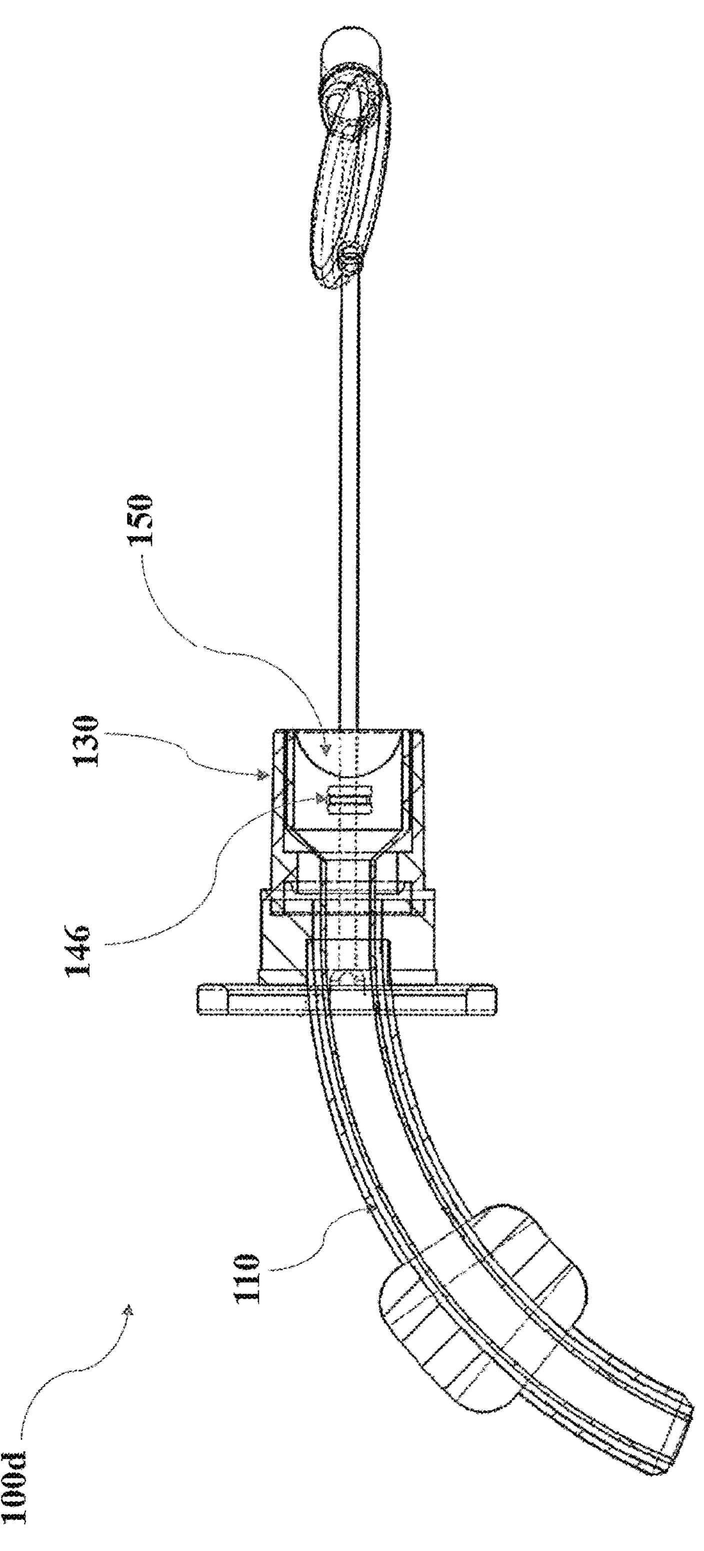
FIG. 5B is a side view of the example tracheostomy tube assembly of FIG. 5A.

FIG. 5A is a perspective view of an example tracheostomy tube assembly 100*d* in which an inner cannula (not labeled in FIG. 5A) has been fully inserted into an outer cannula 110 through an outer cannula connector 130. FIG. 5B is a side view of the example tracheostomy tube assembly 100*d* of FIG. 5A.

The example tracheostomy tube assembly 100*d* of FIG. 5A is substantially the same as or similar to the example tracheostomy tube assembly 100*c* of FIG. 4A, except that the example tracheostomy tube assembly 100*d* of FIG. 5A includes a larger grip protrusion 150 compared to the smaller grip protrusion 148 of the example tracheostomy tube assembly 100*c* of FIG. 4A.

In some embodiments as shown in FIG. 5B, an outer wall of the proximal region 144 of the inner cannula may contact an inner wall of the outer cannula connector 130. In these embodiments, the outer wall of the proximal region 144 of the inner cannula may not be tapered or less tapered than an outer wall of the proximal region 144 of the inner cannula shown in FIG. 4B.

Figure 5C:
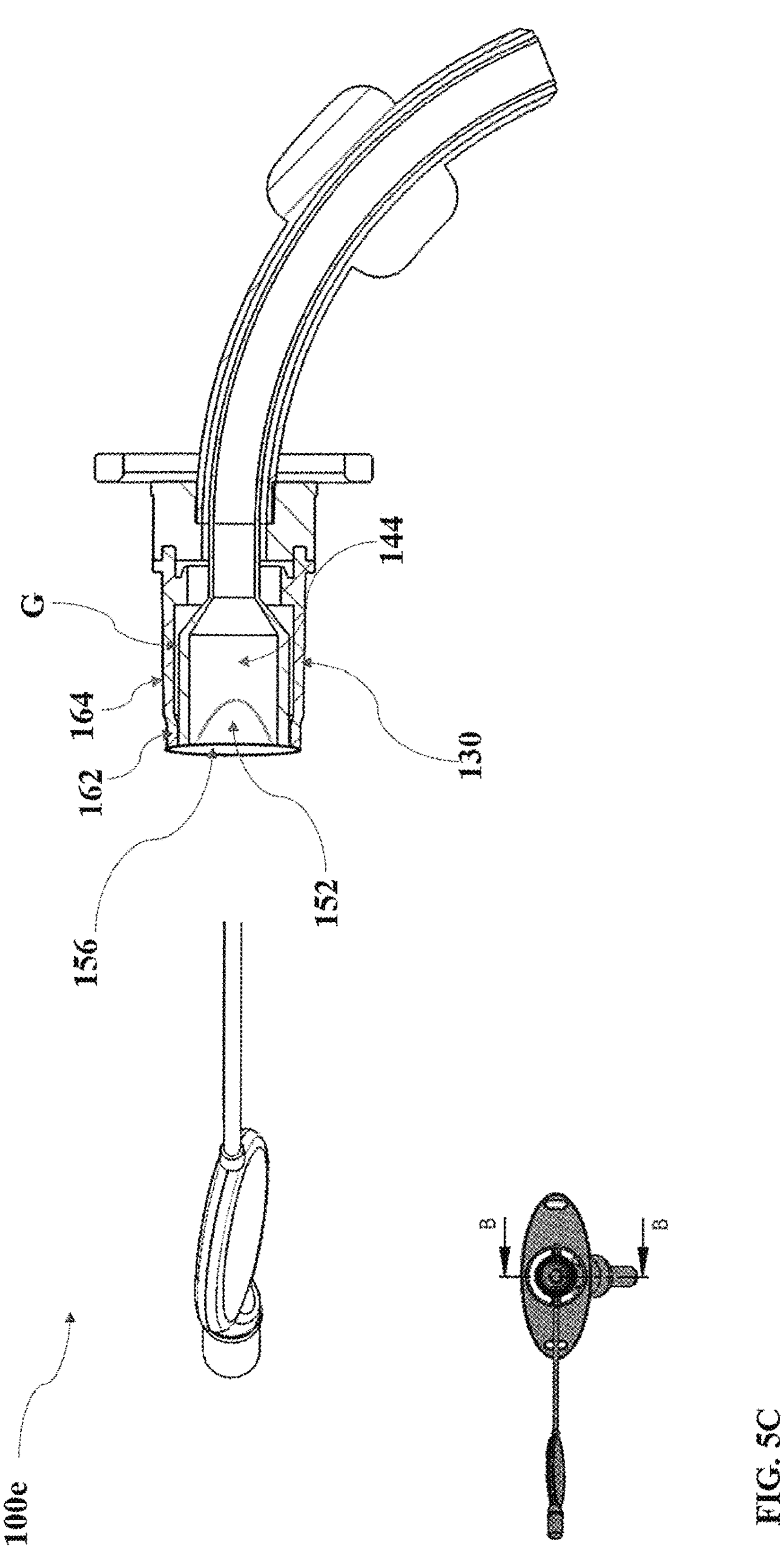
FIGS. 5C-5E are side views of another tracheostomy tube assemblies.
Figure 5D:
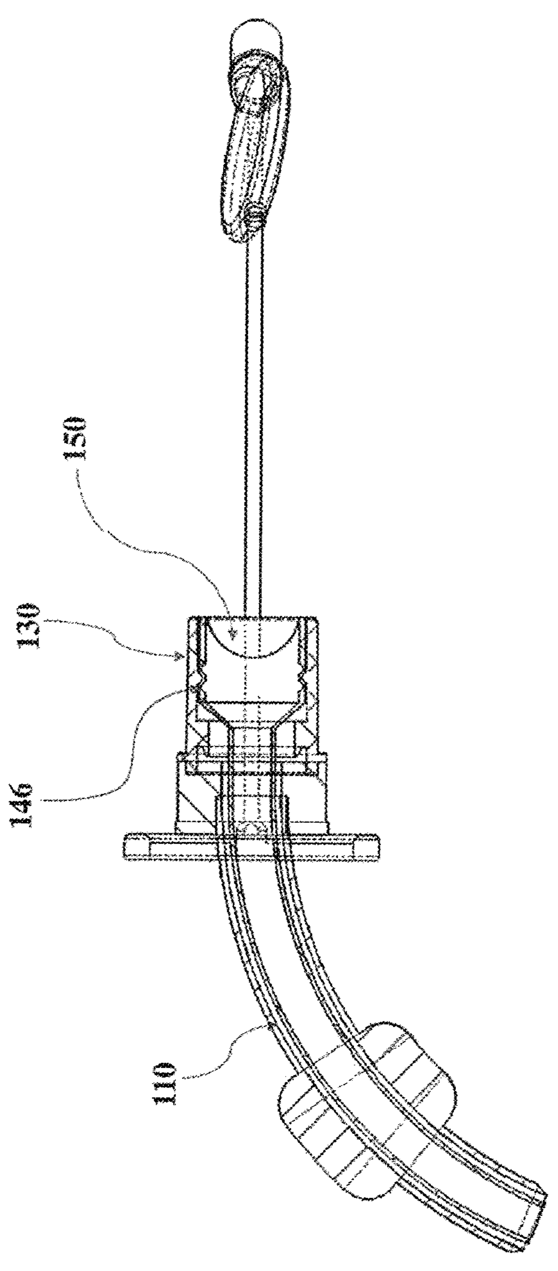
Figure 5D:
Figure 5E:
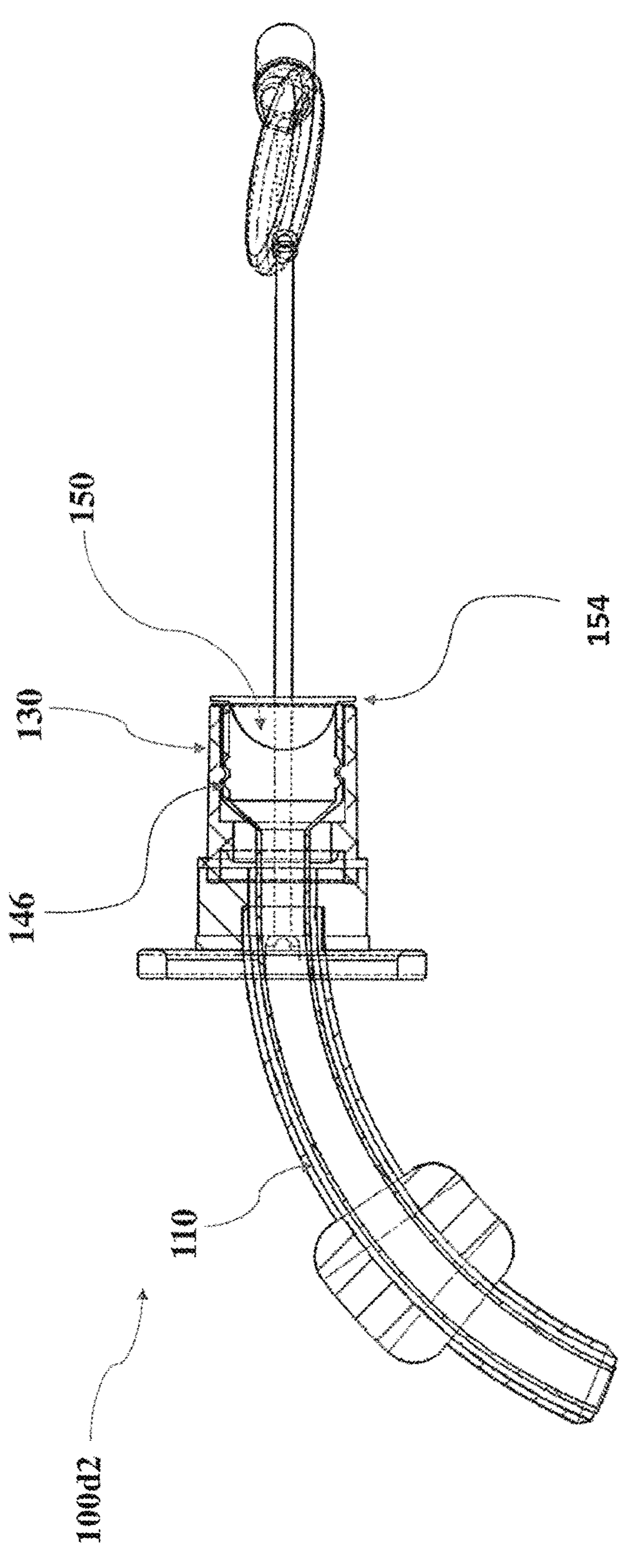

FIG. 5C is a side view of another example tracheostomy tube assembly 100*e*. The example tracheostomy tube assembly 100*e* of FIG. 5C is substantially the same as the example tracheostomy tube assembly 100*d* of FIGS. 5A and 5B, except that the example tracheostomy tube assembly 100*e* of FIG. 5C includes a deeper grip protrusion 152 compared to the grip protrusion 150 of the example tracheostomy tube assembly 100*d* of FIGS. 5A and 5B. In some embodiments, similar to the FIG. 4B embodiment, the outer cannula connector 130 may include a first portion 162 that may contact an outer wall of the proximal region 144 and a second portion 164 that may not contact the outer wall of the proximal region 144 such that there may be a gap (G) formed (in the second portion 164) between the outer wall of the proximal region 144 and the inner wall of the outer cannula connector 130. However, the present disclosure is not limited thereto. For example, similar to the FIG. 5B embodiment, the outer wall of the proximal region 144 of the inner cannula may contact an inner wall of the outer cannula connector 130. For the purpose of convenience, FIG. 5C does not show mating protrusions or recesses.

Figure 6A:
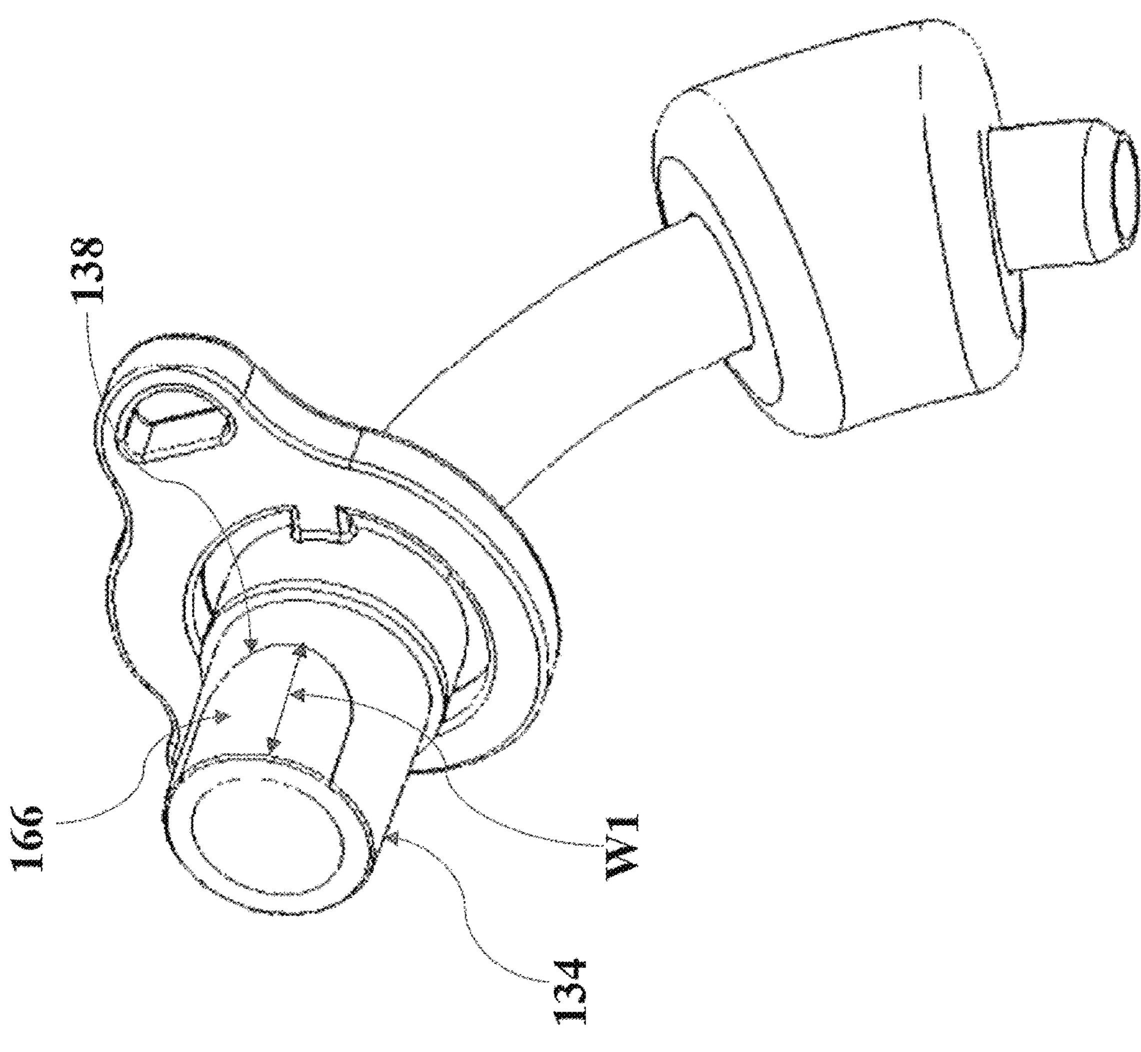
FIG. 6A is a perspective view of another example tracheostomy tube assembly in which an inner cannula is fully inserted into an outer cannula via an outer cannula connector.
Figure 6A:
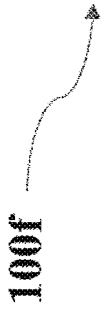
Figure 6B:
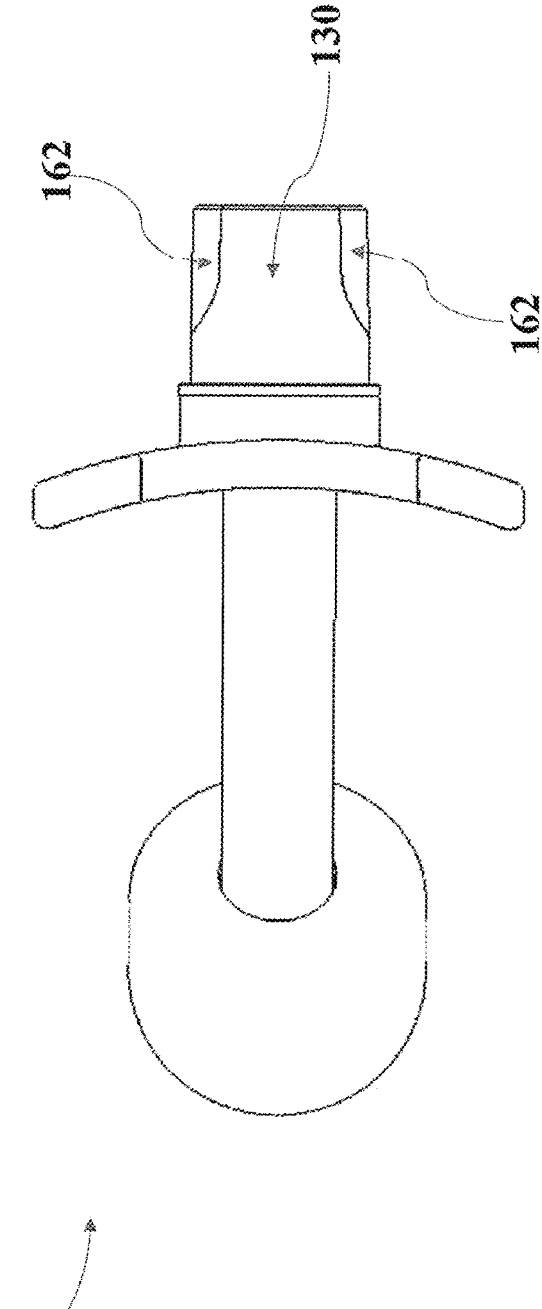
FIG. 6B is a plan view of the tracheostomy tube assembly of FIG. 6A.
Figure 6C:
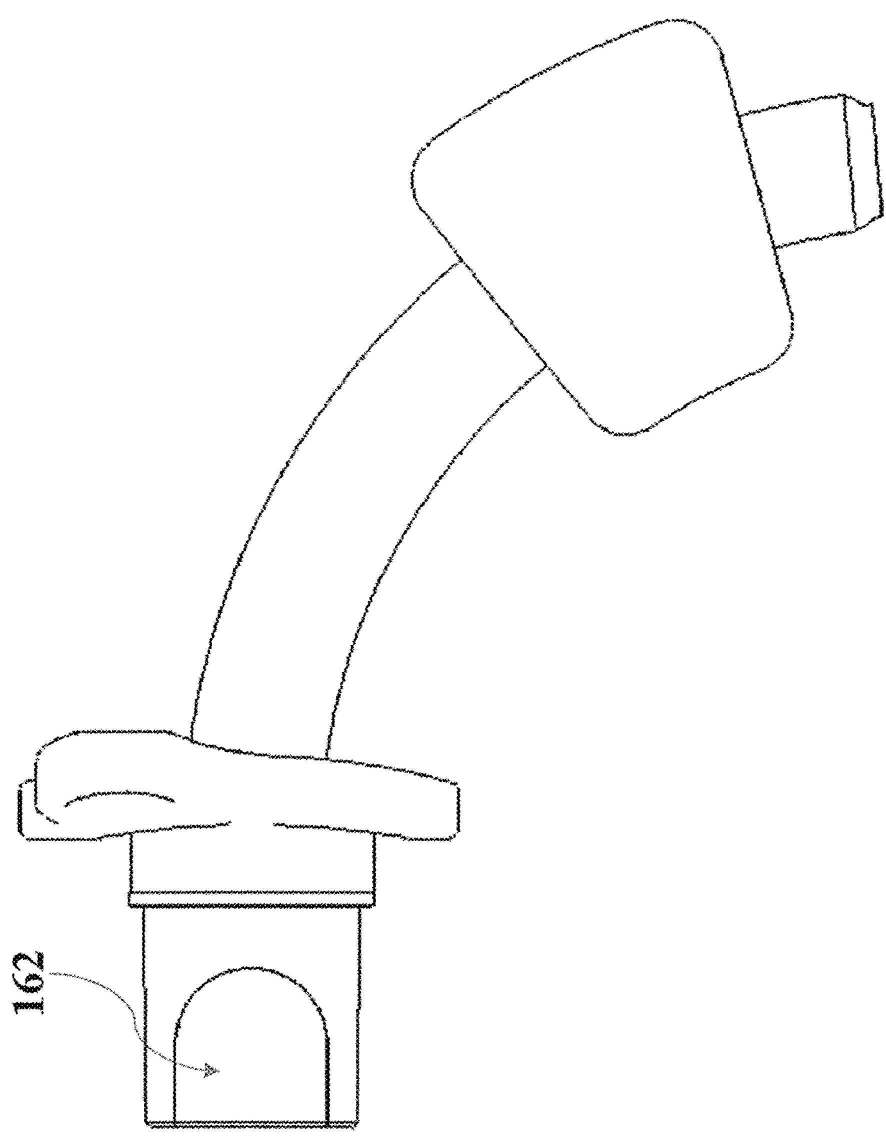
FIG. 6C is a side view of the tracheostomy tube assembly of FIG. 6A.
Figure 6C:
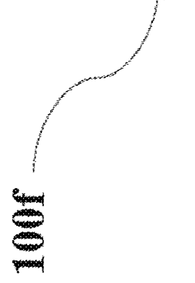

FIG. 6A is a perspective view of an example tracheostomy tube assembly 100*f* in which an inner cannula (not labeled in FIG. 6A) has been fully inserted into an outer cannula 110 through an outer cannula connector 130. FIG. 6B is a plan view of the example tracheostomy tube assembly 100*f* of FIG. 6A. FIG. 6C is a side view of the example tracheostomy tube assembly 100*f* of FIG. 6A.

The example tracheostomy tube assembly 100*f* of FIG. 6A is substantially the same as or similar to the example tracheostomy tube assembly 100*e* of FIG. 5C, except that the example tracheostomy tube assembly 100*f* of FIG. 6A includes a deeper grip protrusion 166 compared to the grip protrusion 152 of the example tracheostomy tube assembly 100*e* of FIG. 5C. In these embodiments, the outer cannula connector 130 may include a deeper cutout 138.

The cutout 138 may include an opening distance similar to that of the FIG. 2B (e.g., between about 8 mm and about 15 mm). The cutout 138 may have a depth (W1) deeper than the depth (W) of the FIG. 2B embodiment. For example, the depth (W1) may be between about 4 mm and about 15 mm (e.g., about 4 mm, about 5 mm, about 6 mm, about 7 mm, about 8 mm, about 9 mm, about 10 mm, about 11 mm, about 12 mm, about 13 mm, about 14 mm, about 15 mm, and ranges between such values). For example, the depth (W1) of the cutout 138 may be between about 6 mm and about 12 mm.

Method of Using Tracheostomy Tube Assembly

Figure 7:
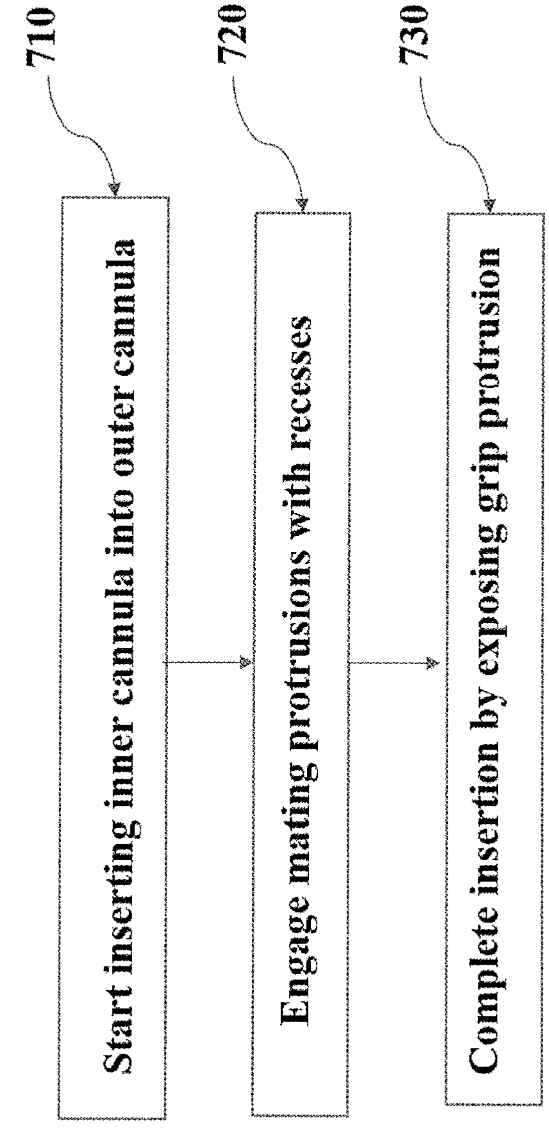
FIG. 7 is a flowchart illustrating a procedure for inserting an inner cannula into an outer cannula via an outer cannula connector.
Figure 7:
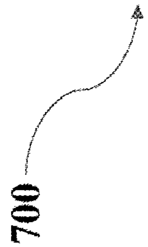

FIG. 7 is a flowchart illustrating an example procedure 700 for using a tracheostomy tube assembly. The example procedure 700 is for inserting an inner cannula into an outer cannula. The procedure illustrated in FIG. 7 is provided for illustrative purposes only. It will be understood that one or more of the steps of the procedure illustrated in FIG. 7 may be removed or that the ordering of the steps may be changed. For the purpose of convenience, the procedure 700 will be explained in connection with the tracheostomy tube assembly 100 shown in FIG. 1. However, the example procedure 700 may be used for other tracheostomy tube assemblies disclosed herein. It is assumed that the tracheostomy tube including the outer cannula 110, the outer cannula connector 130, and the flange are already installed in the trachea, and the procedure 700 is for inserting the inner cannula 140 into the installed tracheostomy tube.

At step 710, a user may start inserting the inner cannula 140 into the outer cannula 110. As disclosed herein, the user may be a patient himself or herself, or a caregiver or a healthcare professional that handles the tracheostomy tube assembly 100 for the patient. In some embodiments, the user may grab or hold at least one of the flange 120 or the outer cannula connector 130 with one hand first. This step may help not move the outer cannula 110, the flange 120, and/or the outer cannula connector 130 so as to stabilize the tracheostomy tube assembly 100 and not to cause discomfort to the user himself (when the user is a patient) or a patient (when the user is a caregiver or a healthcare professional). The user may use his or her left hand or right hand for this step. In a non-limiting example, the user may grab or hold the grip protrusion 148 of the inner cannula 140 with the other hand and insert the inner cannula 140 into the outer cannula 110 through a connector opening 180 (see FIG. 2A) of the outer cannula connector 130. In another non-limiting example, the user may grab or hold the face portion 154 or 156 of the inner cannula 140 with the other hand and insert the inner cannula 140 into the outer cannula 110 through a connector opening 180 (see FIG. 2A) of the outer cannula connector 130. The user may use his right or left hand for this step. The user may initiate inserting the inner cannula 140 into the connector opening 180 while holding the at least one of the flange 120 or the outer cannula connector 130 with one hand and holding the grip protrusion 148 or the face portion 154 or 156 with the other hand.

At step 720, the user may continue to insert the inner cannula 140 until the mating protrusions and/or mating recesses of the inner cannula 140 are engaged with the mating protrusions and/or mating recesses of the outer cannula connector 130. The user may continue to insert the inner cannula 140 into the connector opening 180 while holding the at least one of the flange 120 or the outer cannula connector 130 with one hand and holding the grip protrusion 148 or the face portion 154 or 156 with the other hand. In a non-limiting example, the inner cannula 140 may include one or more mating protrusions and the outer cannula connector 130 may include one or more mating recesses configured to engage with the one or more mating protrusions. In another non-limiting example, the inner cannula 140 may include one or more mating recesses and the outer cannula connector 130 may include one or more mating protrusions configured to engage with the one or more mating recesses. In another non-limiting example, the inner cannula 140 may include two or more mating protrusions and the outer cannula connector 130 may include one or more mating protrusions configured to be latched between the two or more mating protrusions of the inner cannula 140. In another non-limiting example, the outer cannula connector 130 may include two or more mating protrusions and the inner cannula 140 may include one or more mating protrusions and configured to be latched between the two or more mating protrusions of the outer cannula connector 130. The user may feel the engagement between the mating protrusions and recesses, or between two or more protrusions and one or more protrusions.

At step 730, the user may complete insertion of the inner cannula 140 into the outer cannula 110 by exposing the grip protrusion 148 thorough the cutout 132 formed on the outer cannula connector 130. The user may release both of the hands once the inner cannula 140 is fully inserted into the outer cannula 110. The patient may use the tracheostomy tube assembly 100.

Figure 8:
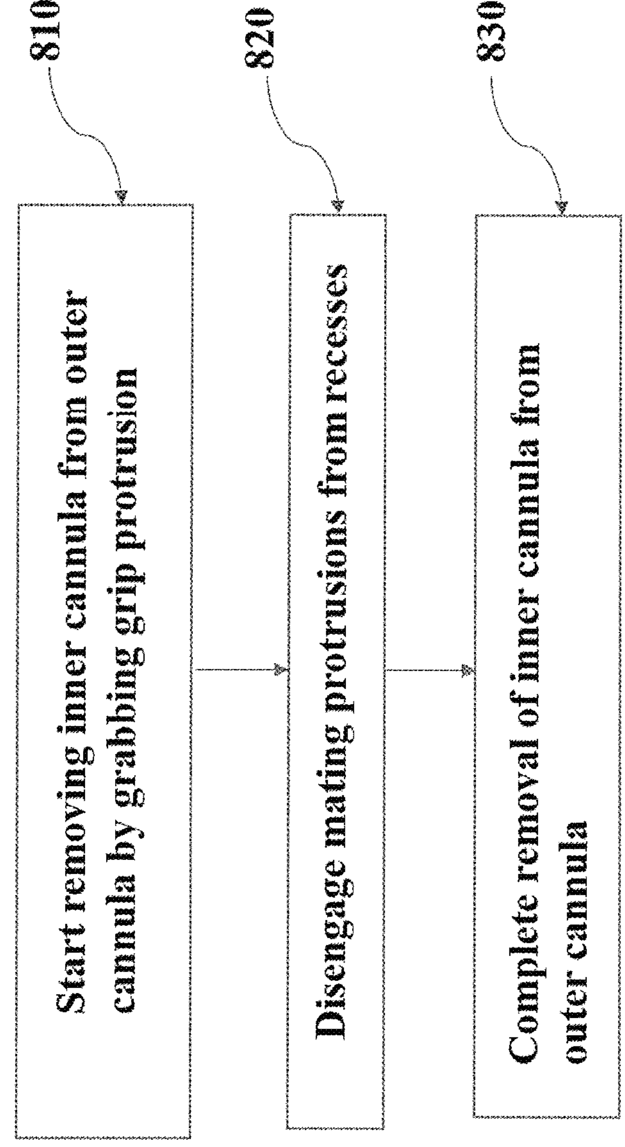
FIG. 8 is a flowchart illustrating a procedure for removing an inner cannula from an outer cannula via an outer cannula connector.
Figure 8:
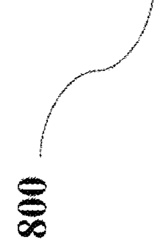

FIG. 8 is a flowchart illustrating another example procedure 800 for using a tracheostomy tube assembly. The example procedure 800 is for removing the inner cannula 140 from the outer cannula 110. The procedure illustrated in FIG. 8 is provided for illustrative purposes only. It will be understood that one or more of the steps of the procedure illustrated in FIG. 8 may be removed or that the ordering of the steps may be changed. For the purpose of convenience, the procedure 800 will be explained in connection with the tracheostomy tube assembly 100 shown in FIG. 1. However, the example procedure 800 may be used for other tracheostomy tube assemblies disclosed herein. The removing procedure 800 of FIG. 8 is generally opposite to the inserting procedure 700 of FIG. 7. It is assumed that the tracheostomy tube assembly 700 including the outer cannula 110, the outer cannula connector 130, the flange 120, and the inner cannula 140 are already installed, and the procedure 800 is for removing the inner cannula 140 from the installed tracheostomy tube assembly 100.

At step 810, the user may start removing the inner cannula 140 from the outer cannula 110. In some embodiments, the user may grab or hold at least one of the flange 120 or the outer cannula connector 130 with one hand (e.g., left or right hand) first to stabilize the tracheostomy tube assembly 100. The user may grab or hold the grip protrusion 148 of the inner cannula 140 (or face portion 154 of FIG. 3E or 156 of FIG. 3F) with the other hand (e.g., right or left hand) and start removing the inner cannula 130 from the outer cannula 110. The user may initiate removing the inner cannula 140 from the outer cannula 110 while holding the at least one of the flange 120 or the outer cannula connector 130 with one hand and holding the grip protrusion 148 or the face portion 154 or 156 with the other hand.

At step 820, the user may continue to remove the inner cannula 140 until the mating protrusions and/or mating recesses of the inner cannula 140 are disengaged from the mating protrusions and/or mating recesses of the outer cannula connector 130. The user may continue to remove the inner cannula 140 from the outer cannula 110 while holding the at least one of the flange 120 or the outer cannula connector 130 with one hand and holding the grip protrusion 148 or the face portion 154 or 156 with the other hand. The user may feel the disengagement of the mating protrusions and recesses, or the disengagement of the two or more protrusions and one or more protrusions.

At step 830, the user may complete removal of the inner cannula 140 from the outer cannula 110. The user may release both of the hands once the inner cannula 140 is fully removed from the outer cannula 110. The user may clean the removed inner cannula 140. The user may put the inner cannula 140 back to the outer cannula 110 after the cleaning is complete.

OTHER EXAMPLES

Various example embodiments of the disclosure can be described by the following clauses:

Clause 1. A tracheal tube assembly comprising: an outer cannula configured to be positioned in a trachea, the outer cannula comprising a distal end and a proximal end, the distal end configured to be disposed inside the trachea, and the proximal end opposing the distal end and configured to be environmentally exposed; an outer cannula connector configured to be coupled to the outer cannula, the outer cannula connector comprising a proximal region, the proximal region comprising a cutout extending in a direction of a length of the outer cannula connector, the outer cannula connector comprising at least one of a non-annular mating recess or a non-annular mating protrusion formed on an inner wall thereof, and the outer cannula connector comprising a connector opening; and an inner cannula comprising a distal region and a proximal region opposing the distal region, the distal region configured to be disposed inside the outer cannula, the proximal region of the inner cannula configured to be inserted into the proximal region of the outer cannula connector via the connector opening, the proximal region of the inner cannula comprising a grip protrusion extending from an outer wall of the proximal region of the inner cannula, the outer wall configured to face the inner wall of the outer cannula connector, the grip protrusion configured to be accommodated at least partially in and exposed by the cutout of the proximal region of the outer cannula connector when the inner cannula is inserted into the outer cannula, and the inner cannula comprising at least one of a non-annular mating protrusion or a non-annular mating recess formed on the outer wall and configured to engage with the at least one of the non-annular mating recess or the non-annular mating protrusion of the outer cannula connector.

Clause 2. The assembly of Clause 1, wherein the grip protrusion is configured to be fully accommodated in the cutout of the proximal region of the outer cannula connector.

Clause 3. The assembly of Clause 1 or 2, wherein the grip protrusion has a dimension substantially the same as the cutout.

Clause 4. The assembly of any of Clauses 1-3, wherein the cutout comprises a first cutout disposed in a first side of the proximal region of the outer cannula connector and a second cutout disposed in a second side of the proximal region of the outer cannula connector, and wherein the grip protrusion comprises a first grip protrusion configured to be accommodated in the first cutout and a second grip protrusion configured to be accommodated in the second cutout.

Clause 5. The assembly of Clause 4, wherein the first side and the second side are opposing each other.

Clause 6. The assembly of Clause 4 or 5, wherein the first grip protrusion and the second grip protrusion are disposed on opposite sides of the outer wall of the proximal region of the inner cannula.

Clause 7. The assembly of any of Clauses 1-6, wherein the grip protrusion comprises a plurality of sets of grip protrusions spaced apart from each other.

Clause 8. The assembly of Clause 7, wherein each of the plurality of sets of grip protrusions comprises two or more grip protrusions.

Clause 9. The assembly of Clause 7, wherein the plurality of sets of grip protrusions comprise a first set of one or more grip protrusions and a second set of one or more grip protrusions spaced apart from each other.

Clause 10. The assembly of Clause 9, wherein the number of the first set of the one or more grip protrusions is different from the number of the second set of the one or more grip protrusions.

Clause 11. The assembly of Clause 9, wherein the number of the first set of the one or more grip protrusions is the same as the number of the second set of the one or more grip protrusions.

Clause 12. The assembly of any of Clauses 7-11, wherein the cutout comprises a plurality of sets of cutouts configured to respectively accommodate the plurality of sets of grip protrusions.

Clause 13. The assembly of any of Clauses 1-12, wherein the non-annular mating recess comprises a plurality of mating recesses that are discontinuous to and separate from each other.

Clause 14. The assembly of Clause 13, wherein the plurality of mating recesses comprise a first non-annular mating recess and a second non-annular mating recess that are disposed on opposite sides of the inner wall of the proximal region of the outer cannula connector.

Clause 15. The assembly of any of Clauses 1-14, wherein the non-annular mating protrusion comprises a plurality of mating protrusions that are discontinuous to and separate from each other.

Clause 16. The assembly of Clause 15, wherein the plurality of mating protrusions comprise a first non-annular mating protrusion and a second non-annular mating protrusion that are disposed on opposite sides of the inner wall of the proximal region of the inner cannula.

Clause 17. The assembly of Clause 15, wherein the plurality of mating protrusions comprise a first set of one or more mating protrusions and a second set of one or more mating protrusions spaced apart from the first set of one or more mating protrusions.

Clause 18. The assembly of any of Clauses 1-17, wherein the proximal region of the outer cannula connector comprises a tapered portion adjacent to the cutout.

Clause 19. The assembly of any of Clauses 1-18, wherein an outer end of the proximal region of the inner canula is configured to be flush with an outer end of the proximal region of the outer cannula connector when the inner cannula is inserted into the outer cannula.

Clause 20. The assembly of any of Clauses 1-19, wherein the grip protrusion is substantially aligned with the mating protrusion in a direction of a length of the inner cannula.

Clause 21. The assembly of any of Clauses 1-20, wherein the grip protrusion is tapered.

Clause 22. The assembly of any of Clauses 1-21, wherein the proximal region of the inner cannula includes a face portion in an outer end thereof, and wherein the face portion is larger in diameter than an adjacent portion of the proximal region of the inner cannula immediately neighboring the face portion.

Clause 23. The assembly of Clause 22, wherein the face portion is configured to rest upon a ridge of the proximal region of the outer cannula connector when the inner cannula is inserted into the outer cannula.

Clause 24. The assembly of any of Clauses 1-23, wherein the proximal region of the inner cannula is tapered.

Clause 25. A tracheal tube assembly comprising: an outer cannula configured to be positioned in a trachea, the outer cannula comprising a distal end and a proximal end, the distal end configured to be disposed inside the trachea, and the proximal end opposing the distal end and configured to be environmentally exposed; an outer cannula connector configured to be coupled to the outer cannula, the outer cannula connector comprising a proximal region, the proximal region comprising a cutout extending in a direction of a length of the outer cannula connector, and the outer cannula connector comprising a connector opening; and an inner cannula comprising a distal region and a proximal region opposing the distal region, the distal region configured to be disposed inside the outer cannula, the proximal region of the inner cannula configured to be inserted into the proximal region of the outer cannula connector via the connector opening, the proximal region of the inner cannula comprising a grip protrusion extending from an outer wall of the proximal region of the inner cannula, the outer wall configured to face the inner wall of the outer cannula connector, the grip protrusion configured to be accommodated at least partially in and exposed by the cutout of the proximal region of the outer cannula connector when the inner cannula is inserted into the outer cannula.

Clause 26. The assembly of Clause 25, wherein the outer cannula connector comprises an inner wall configured to face the outer wall of the proximal region of the inner cannula, wherein the outer cannula connector comprises at least one of a non-annular mating recess or a non-annular mating protrusion formed on the inner wall, and wherein the inner cannula comprises at least one of a non-annular mating protrusion or a non-annular mating recess formed on the outer wall and configured to engage with the at least one of the non-annular mating recess or the non-annular mating protrusion of the outer cannula connector.

Clause 27. The assembly of Clause 26, wherein at least one of the inner wall of the outer cannula connector or the outer wall of the proximal region of the inner cannula is tapered.

Clause 28. The assembly of Clause 27, wherein both of the inner wall of the outer cannula connector and the outer wall of the proximal region of the inner cannula are tapered in opposite directions.

Clause 29. The assembly of any of Clauses 26-28, wherein the grip protrusion is configured to be fully accommodated in the cutout of the proximal region of the outer cannula connector.

Clause 30. The assembly of any of Clauses 26-29, wherein the non-annular mating recess comprises a plurality of sets of mating recesses that are discontinuous to and separate from each other.

Clause 31. The assembly of any of Clauses 26-30, wherein the non-annular mating protrusion comprises a plurality of sets of mating protrusions that are discontinuous to and separate from each other.

Clause 32. A tracheal tube assembly comprising: an outer cannula configured to be positioned in a trachea, the outer cannula comprising a distal end and a proximal end, the distal end configured to be disposed inside the trachea, and the proximal end opposing the distal end and configured to be environmentally exposed; an outer cannula connector configured to be coupled to the outer cannula, the outer cannula connector comprising a proximal region, the outer cannula connector comprising at least one of a non-annular mating recess or a non-annular mating protrusion formed on an inner wall thereof, and the outer cannula connector comprising a connector opening; and an inner cannula comprising a distal region and a proximal region opposing the distal region, the distal region configured to be disposed inside the outer cannula, the proximal region of the inner cannula configured to be inserted into the proximal region of the outer cannula connector via the connector opening, the inner cannula comprising at least one of a non-annular mating protrusion or a non-annular mating recess formed on an outer wall configured to face the inner wall of the outer cannula connector, the at least one of the non-annular mating protrusion or the non-annular mating recess of inner cannula configured to engage with the at least one of the non-annular mating recess or the non-annular mating protrusion of the outer cannula connector, and the proximal region of the inner cannula comprising a face portion in an outer end thereof, the face portion being larger in diameter than an adjacent portion of the proximal region of the inner cannula immediately neighboring the face portion, the face portion configured to rest upon a ridge of the proximal region of the outer cannula connector when the inner cannula is inserted into the outer cannula.

Clause 33. The assembly of Clause 32, wherein the proximal region of the outer cannula connector comprises a cutout extending in a direction of a length of the outer cannula connector, and wherein the proximal region of the inner cannula comprises a grip protrusion extending from the outer wall of the proximal region of the inner cannula, the grip protrusion configured to be accommodated at least partially in and exposed by the cutout of the proximal region of the outer cannula connector when the inner cannula is inserted into the outer cannula.

Clause 34. An inner cannula for a tracheal tube assembly comprising: a body configured to be disposed inside an outer cannula of the tracheal tube assembly, the outer cannula configured to be positioned in a trachea and configured to be coupled to an outer cannula connector, the outer cannula comprising a distal end configured to be disposed inside the trachea and a proximal end opposing the distal end and configured to be environmentally exposed, the outer cannula connector comprising a cutout extending in a direction of a length of the outer cannula connector, and the outer cannula connector comprising at least one of a non-annular mating recess or a non-annular mating protrusion in an inner wall thereof; a head portion extending from the body and configured to be environmentally exposed, the head portion comprising a grip protrusion extending from an outer wall thereof, the grip protrusion configured to be accommodated at least partially in and exposed by the cutout of the outer cannula connector when the body is inserted into the outer cannula and the head portion is inserted into the outer cannula connector; and at least one of a non-annular mating protrusion or a non-annular mating recess formed on the outer wall of the head portion and configured to engage with the at least one of the non-annular mating recess or the non-annular mating protrusion of the outer cannula connector.

Clause 35. The inner cannula of Clause 34, wherein the grip protrusion is configured to be fully accommodated in the cutout.

Clause 36. The inner cannula of Clause 34 or 35, wherein the non-annular mating recess comprises a plurality of sets of mating recesses that are discontinuous to and separate from each other.

Clause 37. The assembly of any of Clauses 34-36, wherein the non-annular mating protrusion comprises a plurality of sets of mating protrusions that are discontinuous to and separate from each other.

Clause 38. A method of using a tracheostomy tube assembly, the method comprising: providing a tracheostomy tube comprising an outer cannula, a flange, and an outer cannula connector, the flange coupled to the outer cannula and outer cannula connector, the outer cannula connector comprising a cutout extending in a direction of a length of the outer cannula connector, the outer cannula connector comprising a connector opening, the outer cannula connector comprising at least one of a non-annular mating recess or a non-annular mating protrusion formed on an inner wall thereof, and the tracheostomy tube installed in a trachea such that the outer cannula is disposed in the trachea and the flange is environmentally exposed and pressed against a neck; providing an inner cannula comprising a proximal region, the proximal region comprising a grip protrusion extending from an outer wall of the proximal region, the outer wall configured to face the inner wall of the outer cannula connector, the inner cannula comprising at least one of a non-annular mating protrusion or a non-annular mating recess formed on the outer wall; initiating insertion of the inner cannula into the outer cannula via the connector opening; engaging the at least one of the non-annular mating protrusion or the mating recess of the inner cannula with the at least one of the non-annular mating recess or the non-annular mating protrusion of the outer cannula connector; and completing insertion of the inner cannula into the outer cannula by exposing the grip protrusion of the inner cannula by the cutout of the outer cannula connector.

Clause 39. The method of Clause 38, wherein the initiating comprises: holding at least one of the flange or the outer cannula connector with one hand; gripping the grip protrusion of the inner cannula with the other hand; and inserting the inner cannula into the outer cannula via the connector opening while holding the at least one of the flange or the outer cannula connector with the one hand and while gripping the grip protrusion of the inner cannula with the other hand.

Clause 40. The method of Clause 39, wherein the grip protrusion comprises two grip protrusions, wherein the cutout comprises two cutouts configured to respectively accommodate the two grip protrusions, and wherein the gripping comprises gripping the two grip protrusions with at least two fingers of the other hand.

Clause 41. The method of any of Clauses 38-40, wherein the inner cannula comprises two or more non-annular mating protrusions, wherein the outer cannula connector comprises two or more non-annular mating recesses, and wherein the engaging comprises engaging the two or more non-annular mating protrusions of the inner cannula with the two or more non-annular mating recesses of the outer cannula connector.

Clause 42. The method of any of Clauses 38-41, wherein the inner cannula comprises two or more non-annular mating protrusions, wherein the outer cannula connector comprises one or more non-annular mating protrusions such that the number of the one or more non-annular mating protrusions is less than the number of the two or more non-annular mating protrusions, and wherein the engaging comprises: engaging the two or more non-annular mating protrusions of the inner cannula with the one or more non-annular mating protrusions of the outer cannula connector such that the one or more non-annular mating protrusions of the outer cannula connector are latched between the two or more non-annular mating protrusions of the inner cannula.

Clause 43. The method of any of Clauses 38-42, wherein the proximal region of the inner cannula comprises a face portion in an outer end thereof, and wherein the face portion is larger in diameter than an adjacent portion of the proximal region immediately neighboring the face portion, wherein the initiating comprises: holding at least one of the flange or the outer cannula connector with one hand; and gripping the face portion of the inner cannula with the other hand inserting the inner cannula into the outer cannula via the connector opening while holding the at least one of the flange or the outer cannula connector with the one hand and while gripping the face portion of the inner cannula with the other hand.

Clause 44. A method of using a tracheostomy tube assembly, the method comprising: providing a tracheostomy tube comprising an outer cannula, a flange, and an outer cannula connector, the flange coupled to the outer cannula and outer cannula connector, the outer cannula connector comprising a cutout extending in a direction of a length of the outer cannula connector, the outer cannula connector comprising a connector opening, and the tracheostomy tube installed in a trachea such that the outer cannula is disposed in the trachea and the flange is environmentally exposed and pressed against a neck; providing an inner cannula comprising a proximal region, the proximal region comprising a grip protrusion extending from an outer wall of the proximal region, the outer wall configured to face the inner wall of the outer cannula connector; initiating insertion of the inner cannula into the outer cannula via the connector opening; and completing insertion of the inner cannula into the outer cannula by exposing the grip protrusion of the inner cannula by the cutout of the outer cannula connector.

Clause 45. The method of Clause 44, wherein the outer cannula connector comprises at least one of a non-annular mating recess or a non-annular mating protrusion formed on an inner wall thereof, and wherein the inner cannula comprises at least one of a non-annular mating protrusion or a non-annular mating recess formed on an outer wall thereof facing the inner wall, the method further comprising, prior to the completing: engaging the at least one of the non-annular mating protrusion or the mating recess of the inner cannula with the at least one of the non-annular mating recess or the non-annular mating protrusion of the outer cannula connector.

Clause 46. The method of Clause 45, wherein the initiating comprises: holding at least one of the flange or the outer cannula connector with one hand; gripping the grip protrusion of the inner cannula with the other hand; and inserting the inner cannula into the outer cannula via the connector opening while holding the at least one of the flange or the outer cannula connector with the one hand and while gripping the grip protrusion of the inner cannula with the other hand.

Clause 47. The method of Clause 45 or 46, wherein the grip protrusion comprises two grip protrusions, wherein the cutout comprises two cutouts configured to respectively accommodate the two grip protrusions, and wherein the gripping comprises gripping the two grip protrusions with at least two fingers of the other hand.

Clause 48. The method of any of Clauses 44-47, wherein the proximal region of the inner cannula comprises a face portion in an outer end thereof, wherein the face portion is larger in diameter than an adjacent portion of the proximal region immediately neighboring the face portion, and wherein the initiating comprises: holding at least one of the flange or the outer cannula connector with one hand; gripping the face portion of the inner cannula with the other hand; and inserting the inner cannula into the outer cannula via the connector opening while holding the at least one of the flange or the outer cannula connector with the one hand and while gripping the face portion of the inner cannula with the other hand.

Clause 49. A method of using a tracheostomy tube assembly, the method comprising: providing a tracheostomy tube assembly placed in a trachea, the tracheostomy tube assembly comprising an outer cannula, a flange, an outer cannula connector, and an inner cannula, the flange supporting the outer cannula and outer cannula connector, the outer cannula connector coupled to the outer cannula and comprising a connector opening, the outer cannula connector comprising a cutout extending in a direction of a length of the outer cannula connector, the outer cannula connector comprising at least one of a non-annular mating recess or a non-annular mating protrusion formed on an inner wall thereof, the inner cannula disposed inside the outer cannula and outer cannula connector, the inner cannula comprising a proximal region, the proximal region of the inner cannula comprising a grip protrusion, the inner cannula comprising at least one of a non-annular mating protrusion or a non-annular mating recess formed on an outer wall of the proximal region, and the outer wall configured to face the inner wall of the outer cannula connector; initiating removal of the inner cannula from the outer cannula; disengaging the at least one of the non-annular mating protrusion or the mating recess of the inner cannula from the at least one of the non-annular mating recess or the non-annular mating protrusion of the outer cannula connector; and completing removal of the inner cannula from the outer cannula by separating the inner cannula from the outer cannula connector.

Clause 50. The method of Clause 49, wherein the initiating comprises: holding at least one of the flange or the outer cannula connector with one hand; gripping the grip protrusion of the inner cannula with the other hand; and removing the inner cannula from the outer cannula while holding the at least one of the flange or the outer cannula connector with the one hand and while gripping the grip protrusion of the inner cannula with the other hand.

Clause 51. The method of Clause 49 or 50, wherein the grip protrusion comprises two grip protrusions, wherein the cutout comprises two cutouts configured to respectively accommodate the two grip protrusions, and wherein the gripping comprises gripping the two grip protrusions with at least two fingers of the other hand.

Clause 52. The method of any of Clauses 49-51, wherein the inner cannula comprises two or more non-annular mating protrusions, wherein the outer cannula connector comprises two or more non-annular mating recesses, and wherein the engaging comprises engaging the two or more non-annular mating protrusions of the inner cannula with the two or more non-annular mating recesses of the outer cannula connector.

Clause 53. The method of any of Clauses 49-52, wherein the inner cannula comprises two or more non-annular mating protrusions, wherein the outer cannula connector comprises one or more non-annular mating protrusions, and wherein the engaging comprises engaging the two or more non-annular mating protrusions of the inner cannula with the one or more non-annular mating protrusions of the outer cannula connector such that the one or more non-annular mating protrusions of the outer cannula connector are latched between the two or more non-annular mating protrusions of the inner cannula.

Clause 54. The method of any of Clauses 49-53, wherein the proximal region of the inner cannula comprises a face portion in an outer end thereof, wherein the face portion is larger in diameter than an adjacent portion of the proximal region immediately neighboring the face portion, and wherein the initiating comprises: holding at least one of the flange or the outer cannula connector with one hand; gripping the face portion of the inner cannula with the other hand; and removing the inner cannula from the outer cannula while holding the at least one of the flange or the outer cannula connector with the one hand and while gripping the face portion of the inner cannula with the other hand.

Clause 55. A method of using a tracheostomy tube assembly, the method comprising: providing a tracheostomy tube assembly placed in a trachea, the tracheostomy tube assembly comprising an outer cannula, a flange, an outer cannula connector, and an inner cannula, the flange supporting the outer cannula and outer cannula connector, the outer cannula connector coupled to the outer cannula and comprising a connector opening, the outer cannula connector comprising a cutout extending in a direction of a length of the outer cannula connector, the inner cannula disposed inside the outer cannula and outer cannula connector, the inner cannula comprising a proximal region, and the proximal region of the inner cannula comprising a grip protrusion extending from an outer wall of the proximal region; initiating removal of the inner cannula from the outer cannula; and completing removal of the inner cannula from the outer cannula by separating the inner cannula from the outer cannula connector.

Clause 56. The method of Clause 55, wherein the outer cannula connector comprises at least one of a non-annular mating recess or a non-annular mating protrusion formed on an inner wall thereof, and wherein the inner cannula comprises at least one of a non-annular mating protrusion or a non-annular mating recess formed on an outer wall of the proximal region, the method comprising: disengaging at least one of the non-annular mating protrusion or the mating recess of the inner cannula from at least one of the non-annular mating recess or the non-annular mating protrusion of the outer cannula connector.

Clause 57. The method of Clause 55 or 56, wherein the initiating comprises: holding at least one of the flange or the outer cannula connector with one hand; gripping the grip protrusion of the inner cannula with the other hand; and removing the inner cannula from the outer cannula while holding the at least one of the flange or the outer cannula connector with the one hand and while gripping the grip protrusion of the inner cannula with the other hand.

Clause 58. The method of any of Clauses 55-57, wherein the grip protrusion comprises two grip protrusions, wherein the cutout comprises two cutouts configured to respectively accommodate the two grip protrusions, and wherein gripping the grip protrusion comprises gripping the two grip protrusions with at least two fingers of the other hand.

Clause 59. The method of any of Clauses 55-58, wherein the proximal region of the inner cannula comprises a face portion in an outer end thereof, wherein the face portion is larger in diameter than an adjacent portion of the proximal region immediately neighboring the face portion, and wherein the initiating comprises: holding at least one of the flange or the outer cannula connector with one hand; gripping the face portion of the inner cannula with the other hand; and removing the inner cannula from the outer cannula while holding the at least one of the flange or the outer cannula connector with the one hand and while gripping the face portion of the inner cannula with the other hand.

Clause 60. A tracheal tube assembly kit comprising: an outer cannula configured to be positioned in a trachea, the outer cannula comprising a distal end and a proximal end, the distal end configured to be disposed inside the trachea, the proximal end opposing the distal end and configured to be environmentally exposed; an outer cannula connector configured to be coupled to the outer cannula, the outer cannula connector comprising a proximal region, the proximal region comprising a cutout extending in a direction of a length of the outer cannula connector, the outer cannula connector comprising a connector opening; and an inner cannula comprising a distal region and a proximal region opposing the distal region, the distal region configured to be disposed inside the outer cannula, the proximal region of the inner cannula configured to be inserted into the proximal region of the outer cannula connector via the connector opening, the proximal region of the inner cannula comprising a grip protrusion extending from an outer wall of the proximal region of the inner cannula, the grip protrusion configured to be accommodated at least partially in and exposed by the cutout of the proximal region of the outer cannula connector when the inner cannula is inserted into the outer cannula, the inner cannula comprising at least one of a non-annular mating protrusion or a non-annular mating recess formed on an outer wall of the proximal region, the outer cannula connector comprising an inner wall configured to face the outer wall of the proximal region of the inner cannula, and the outer cannula connector comprising at least one of a non-annular mating recess or a non-annular mating protrusion formed on the inner wall configured to engage with the at least one of the non-annular mating protrusion or the non-annular mating recess of the inner cannula.

Clause 61. A tracheal tube assembly kit comprising: an outer cannula configured to be positioned in a trachea, the outer cannula comprising a distal end and a proximal end, the distal end configured to be disposed inside the trachea, the proximal end opposing the distal end and configured to be environmentally exposed; an outer cannula connector configured to be coupled to the outer cannula, the outer cannula connector comprising a proximal region, the proximal region comprising a cutout extending in a direction of a length of the outer cannula connector, the outer cannula connector comprising a connector opening; and an inner cannula comprising a distal region and a proximal region opposing the distal region, the distal region configured to be disposed inside the outer cannula, the proximal region of the inner cannula configured to be inserted into the proximal region of the outer cannula connector via the connector opening, the proximal region of the inner cannula comprising a grip protrusion extending from an outer wall of the proximal region of the inner cannula, and the grip protrusion configured to be accommodated at least partially in and exposed by the cutout of the proximal region of the outer cannula connector when the inner cannula is inserted into the outer cannula.

Although certain embodiments are described herein with a set of mating features on the inner cannula and another set of mating features on the outer cannula, it should be understood that the features on the inner cannula and the outer cannula could be reversed. For example, although certain embodiments are described with a mating recess on the outer cannula and a mating protrusion on the inner cannula, it is imaginable that the mating recess could be on the inner cannula and the mating projection on the outer cannula. Moreover, although certain embodiments are described with a single mating feature on the outer cannula interfacing with a pair of mating features on the inner cannula, this arrangement could be reversed.

Conditional language used herein, such as, among others, "can," "could," "might," "may," "e.g.," and the like, unless specifically stated otherwise, or otherwise understood within the context as used, is generally intended to convey that certain embodiments include, while some embodiments do not include, certain features, elements and/or steps. The terms "comprising," "including," "having," and the like are synonymous and are used inclusively, in an open-ended fashion, and do not exclude additional elements, features, acts, operations, and so forth.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 0.3 inches" should include "0.3 inches." Phrases preceded by a term such as "substantially" include the recited phrase and should be interpreted based on the circumstances (e.g., as much as reasonably possible under the circumstances). For example, "substantially cover" includes "fully cover." Unless stated otherwise, all measurements are at standard conditions including temperature and pressure. The phrase "at least one of" is intended to require at least one item from the subsequent listing, not one type of each item from each item in the subsequent listing. For example, "at least one of A, B, and C" can include A, B, C, A and B, A and C, B and C, or A, B, and C.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, and at least one of Z is present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

The methods disclosed herein may include certain actions taken by a practitioner; however, the methods can also include any third-party instruction of those actions, either expressly or by implication. For example actions such as "coupling the tracheostomy occlusion adapter to the tracheostomy tube" include "instructing coupling of the tracheostomy occlusion adapter to the tracheostomy tube."

What is claimed is:

1. A tracheostomy tube assembly comprising:

an outer cannula configured to be positioned in a trachea,
  the outer cannula comprising a distal end and a proximal end,
  the distal end configured to be disposed inside the trachea, and
  the proximal end opposing the distal end and configured to be environmentally exposed;

an outer cannula connector configured to be coupled to the outer cannula,
  the outer cannula connector comprising a proximal region,
  the proximal region comprising a cutout extending in a direction of a length of the outer cannula connector,
  the outer cannula connector comprising at least one of a non-annular mating recess or a non-annular mating protrusion formed on an inner wall thereof, and
  the outer cannula connector comprising a connector opening; and an inner cannula comprising a body and a head portion,
  the body configured to be disposed inside the outer cannula,
  the head portion configured to be inserted into the proximal region of the outer cannula connector via the connector opening,
  the head portion comprising a grip protrusion radially outwardly extending from an outer wall of the head portion of the inner cannula such that the grip protrusion protrudes from the outer wall of the head portion, the grip protrusion configured to be gripped by a finger and exposed to the environment, the outer wall configured to face the inner wall of the outer cannula connector, wherein the grip protrusion is tapered in a direction extending toward the body of the inner cannula and matches a contour of the cutout,
  the head portion comprising an occlusion opening at an outer end,
  the head portion configured such that the occlusion opening enables a user to occlude the tracheostomy tube assembly by sealing the occlusion opening with a finger,
  the grip protrusion configured to be accommodated at least partially in and exposed by the cutout of the proximal region of the outer cannula connector when the inner cannula is inserted into the outer cannula, and the inner cannula comprising at least one of a non-annular mating protrusion or a non-annular mating recess formed on the outer wall and configured to engage with at least one of the non-annular mating recess or the non-annular mating protrusion of the outer cannula connector.

2. The assembly of claim 1, wherein the grip protrusion is configured to be fully accommodated in the cutout of the proximal region of the outer cannula connector.

3. The assembly of claim 1, wherein the grip protrusion has a dimension substantially the same as the cutout.

4. The assembly of claim 1, wherein the cutout comprises a first cutout disposed in a first side of the proximal region of the outer cannula connector and a second cutout disposed in a second side of the proximal region of the outer cannula connector, and wherein the grip protrusion comprises a first grip protrusion configured to be accommodated in the first cutout and a second grip protrusion configured to be accommodated in the second cutout.

5. The assembly of claim 4, wherein the first side and the second side are opposing each other.

6. The assembly of claim 4, wherein the first grip protrusion and the second grip protrusion are disposed on opposite sides of the outer wall of the head portion of the inner cannula.

7. The assembly of claim 1, wherein the grip protrusion comprises a plurality of sets of grip protrusions spaced apart from each other.

8. The assembly of claim 7, wherein each of the plurality of sets of grip protrusions comprises two or more grip protrusions.

9. The assembly of claim 7, wherein the plurality of sets of grip protrusions comprise a first set of one or more grip protrusions and a second set of one or more grip protrusions spaced apart from each other.

10. The assembly of claim 9, wherein the number of the first set of the one or more grip protrusions is different from the number of the second set of the one or more grip protrusions.

11. The assembly of claim 9, wherein the number of the first set of the one or more grip protrusions is the same as the number of the second set of the one or more grip protrusions.

12. The assembly of claim 7, wherein the cutout comprises a plurality of sets of cutouts configured to respectively accommodate the plurality of sets of grip protrusions.

13. The assembly of claim 1, wherein the at least one non-annular mating recess of the outer cannula connector comprises a plurality of mating recesses that are discontinuous to and separate from each other.

14. The assembly of claim 13, wherein the plurality of mating recesses comprise a first non-annular mating recess and a second non-annular mating recess that are disposed on opposite sides of the inner wall of the proximal region of the outer cannula connector.

15. The assembly of claim 1, wherein the at least one non-annular mating protrusion of the inner cannula comprises a plurality of mating protrusions that are discontinuous to and separate from each other.

16. The assembly of claim 15, wherein the plurality of mating protrusions comprise a first non-annular mating protrusion and a second non-annular mating protrusion that are disposed on opposite sides of the outer wall of the head portion of the inner cannula.

17. The assembly of claim 15, wherein the plurality of mating protrusions comprise a first set of one or more mating protrusions and a second set of one or more mating protrusions spaced apart from the first set of one or more mating protrusions.

18. The assembly of claim 1, wherein the proximal region of the outer cannula connector comprises a tapered portion adjacent to the cutout.

19. The assembly of claim 1, wherein the outer end of the head portion of the inner canula is configured to be flush with an outer end of the proximal region of the outer cannula connector when the inner cannula is inserted into the outer cannula.

20. The assembly of claim 1, wherein the grip protrusion is substantially aligned with the at least one non-annular mating protrusion of the inner cannula or the at least one non-annular mating protrusion of the outer cannular connector in a direction of a length of the inner cannula.

21. The assembly of claim 1, wherein the head portion of the inner cannula includes a face portion in the outer end thereof, and wherein the face portion is larger in diameter than an adjacent portion of the head portion of the inner cannula immediately neighboring the face portion.

22. The assembly of claim 21, wherein the outer cannula connector comprises a ridge in the proximal region thereof circumferentially neighboring the cutout, and wherein the face portion is configured to rest upon the ridge when the inner cannula is inserted into the outer cannula.

23. The assembly of claim 1, wherein the head portion of the inner cannula is tapered in a direction extending toward the body of the inner cannula.

24. The assembly of claim 22, wherein the ridge is tapered and becomes gradually thinner in a direction extending toward a distal region of the outer cannula connector.

25. The assembly of claim 1, wherein the grip protrusion has a height measured from the outer wall of the head portion in a range of about 0.5 mm and about 3.5 mm.

26. The assembly of claim 1, wherein the grip protrusion is not aligned with the at least one non-annular mating protrusion of the inner cannula or the at least one non-annular mating protrusion of the outer cannular connector in a direction of a length of the inner cannula.

* * * * *